(12) United States Patent
Tolan et al.

(10) Patent No.: US 8,202,709 B2
(45) Date of Patent: Jun. 19, 2012

(54) ENZYME COMPOSITIONS AND METHODS FOR THE IMPROVED ENZYMATIC HYDROLYSIS OF CELLULOSE

(75) Inventors: Jeffrey Tolan, Ontario (CA); Theresa White, Ontario (CA); John Tomashek, Ontario (CA)

(73) Assignee: Iogen Energy Corporation, Ontario (CA)

( * ) Notice: Subject to any disclaimer, the term of this patent is extended or adjusted under 35 U.S.C. 154(b) by 504 days.

(21) Appl. No.: 12/305,069

(22) PCT Filed: Jun. 22, 2007

(86) PCT No.: PCT/CA2007/001132
§ 371 (c)(1),
(2), (4) Date: Apr. 3, 2009

(87) PCT Pub. No.: WO2007/147263
PCT Pub. Date: Dec. 27, 2007

(65) Prior Publication Data
US 2010/0068768 A1    Mar. 18, 2010

Related U.S. Application Data

(60) Provisional application No. 60/815,891, filed on Jun. 22, 2006.

(51) Int. Cl.
*C12P 19/14* (2006.01)
*C12N 9/42* (2006.01)
*C12N 9/24* (2006.01)
*C02F 3/34* (2006.01)
*C08B 37/00* (2006.01)

(52) U.S. Cl. .......... 435/99; 435/209; 435/200; 435/262; 435/274

(58) Field of Classification Search .................... 435/99, 435/209, 200, 262, 274
See application file for complete search history.

(56) References Cited

U.S. PATENT DOCUMENTS

| | | | |
|---|---|---|---|
| 3,972,775 A | | 8/1976 | Wilke et al. |
| 4,461,648 A | | 7/1984 | Foody |
| 5,719,044 A | * | 2/1998 | Shoseyov et al. ............ 435/69.7 |
| 5,763,254 A | | 6/1998 | Woldike et al. |
| 5,856,201 A | | 1/1999 | Shoseyov et al. |
| 5,962,289 A | | 10/1999 | Kilburn et al. |
| 2006/0154352 A1 | * | 7/2006 | Foody et al. ................... 435/161 |

FOREIGN PATENT DOCUMENTS

| | | |
|---|---|---|
| WO | 94/29460 | 12/1994 |
| WO | 2005/118828 | 12/2005 |
| WO | WO 2006/063467 A1 * | 6/2006 |

OTHER PUBLICATIONS

Lymar et al., "Purification and Characterization of a Cellulose-Binding (β-Glucosidase from Cellulose-Degrading Cultures of *Phanerochaete chrysosporium*", Applied and Environmental Microbiology, vol. 61, No. 8 (1995) 2976-80.
Ahn et al., "Imobilization of β-glucosidase using the cellulose-binding domain of *Bacillus subtilis* endo-β-1, 4-glucanase", Biotechnology Letters, vol. 19, No. 5 (1997) 483-86.
Teeri et al., "Cellulose degradation by native and engineered fungal cellulases", Carbohydrates in Europe, vol. 12 (1995) 28-33.
Alfani, "Membrane Reactors for the Investigation of Product Inhibition of Enzyme Activity", Journal of Membrane Science, vol. 52 (1990) 339-50.
Ghosh, et al., "Simultaneous saccharification and fermentation of cellulose: effect of β-D-glucosidase activity and ethanol inhibition of cellulases", Enzyme Microb. Technol., vol. 4 (1982) 425-30.
Tolan, "Iogen's Demonstration Process for Producing Ethanol from Cellulosic Biomass", Fuel-oriented Biorefineries, vol. 1, Ch. 9, 193-207, 2002.
Ohlson, et al., "Enzymatic Hydrolysis of Sodium-Hydroxide-Pretreatment Sallow in an Ultrafiltration Membrane Reactor", Biotechnology and Bioengineering, vol. 26 (1984) 647-53.
Ishihara, et al., "Semicontinuous Enzymatic Hydrolysis of Lignocelluloses", Biotechnolgy and Bioengineering, vol. 37 (1991) 948-54.
Tan, et al., "Column cellulose hydrolysis reactor: Cellulase adsorption profile", Appl. Microbiol. Biotechnol., vol. 25 (1986) 256-61.
Knutsen, et al., "Combined Sedimentation and Filtration Process for Cellulase Recovery During Hydrolysis of Lignocellulosic Biomass", Applied Biochemistry and Biotechnology, vol. 98-100 (2002) 1161-72.
Mores, et al., "Cellulase Recovery via Membrane Filtration" Applied Biochemistry and Biotechnology, vol. 91-93 (2001) 297-309.
Ramos, et al., "The use of enzyme recycling and the influence of sugar accumulation on cellulose hydrolysis by *Trichoderma* cellulases", Enzyme Microb. Technol., vol. 15 (1993) 19-25.
Lee, et al., "Evaluation of Cellulase Recycling Strategies for the Hydrolysis of Lignocellulosic Substrates", Biotechnology and Bioengineering, vol. 45 (1995) 328-36.
Tu, et al., "Immobilization of β-glucosidase on Eupergit C for lignocellulose hydrolysis", Biotechnol. Lett., vol. 28 (2006) 151-56.
Howard, et al., "Lignocellulose biotechnology: issues of bioconverstion and enzyme production", African Journal of Biotechnology, vol. 2, No. 12 (2003) 602-19.

* cited by examiner

*Primary Examiner* — Ganapathirama Raghu
(74) *Attorney, Agent, or Firm* — Fitzpatrick, Cella, Harper & Scinto

(57) ABSTRACT

A process for the enzymatic hydrolysis of cellulose to produce a hydrolysis product comprising glucose from a pretreated lignocellulosic feedstock and enzymes for use in the process are provided. The process comprises partially hydrolyzing an aqueous slurry of a pretreated lignocellulosic feedstock with cellulase enzymes, one or more than one β-glucosidase enzyme and a binding agent for binding the β-glucosidase enzyme to fiber solids present in the aqueous slurry. The unhydrolyzed fiber solids are then separated from the hydrolyzed slurry. The separated fiber solids thus obtained are then re-suspended in an aqueous solution to produce a re-suspended slurry. The hydrolysis is then continued to produce the hydrolysis product comprising glucose.

22 Claims, 5 Drawing Sheets

ENZYME COMPOSITIONS AND METHODS FOR THE IMPROVED ENZYMATIC HYDROLYSIS OF CELLULOSE

FIELD OF INVENTION

The present invention relates to enzymes for the hydrolysis of cellulose and methods of using same. More specifically, the present invention relates to cellulase and β-glucosidase enzymes for the enzymatic hydrolysis of cellulose to produce a hydrolysis product comprising glucose from a pretreated lignocellulosic feedstock.

BACKGROUND OF THE INVENTION

Fuel ethanol is currently produced from feedstocks such as corn starch, sugar cane, and sugar beets. However, the potential for production of ethanol from these sources is limited as most of the farmland which is suitable for the production of these crops is already in use as a food source for humans. Furthermore, the production of ethanol from these feedstocks has a negative impact on the environment because fossil fuels used in the conversion process produce carbon dioxide and other byproducts.

The production of ethanol from cellulose-containing feedstocks, such as agricultural wastes, grasses, and forestry wastes, has received much attention in recent years. The reasons for this are because these feedstocks are widely available and inexpensive and their use for ethanol production provides an alternative to burning or landfilling lignocellulosic waste materials. Moreover, a byproduct of cellulose conversion, lignin, can be used as a fuel to power the process instead of fossil fuels. Several studies have concluded that, when the entire production and consumption cycle is taken into account, the use of ethanol produced from cellulose generates close to nil greenhouse gases.

The cellulosic feedstocks that are the most promising for ethanol production include (1) agricultural wastes such as corn stover, corn cobs, corn fiber, wheat straw, barley straw, oat straw, oat hulls, rice straw, rice hulls, canola straw, and soybean stover; (2) grasses such as switch grass, miscanthus, cord grass, rye grass and reed canary grass; (3) forestry biomass such as recycled wood pulp fiber, softwood, hardwood and sawdust; and (4) sugar processing residues such as bagasse and beet pulp.

The first process step of converting lignocellulosic feedstock to ethanol involves breaking down the fibrous material to liberate sugar monomers, such as glucose, from the feedstock for conversion to ethanol in the subsequent step of fermentation. The two primary processes are acid hydrolysis, which involves the hydrolysis of the feedstock using a single step of acid treatment, and enzymatic hydrolysis, which involves an acid pretreatment followed by hydrolysis with cellulase enzymes.

In the acid hydrolysis process, the feedstock is subjected to steam and a strong acid, such as sulfuric acid, at a temperature, acid concentration and length of time that are sufficient to hydrolyze the cellulose to glucose and hemicellulose to xylose and arabinose. In the case when sulfuric acid is used, the acid can be concentrated (25-80% w/w) or dilute (3-8% w/w), measured as the weight of acid in the weight of acidified aqueous solution that is present with the feedstock. The glucose is then fermented to ethanol using yeast, and the ethanol is recovered and purified by distillation.

In the enzymatic hydrolysis process, the steam temperature, acid concentration and treatment time are chosen to be milder than that in the acid hydrolysis process such that the cellulose surface area is greatly increased as the fibrous feedstock is converted to a muddy texture, but there is little conversion of the cellulose to glucose. The pretreated cellulose is then hydrolyzed to glucose in a subsequent step that uses cellulase enzymes, and the steam/acid treatment in this case is known as pretreatment. Prior to the addition of enzyme, the pH of the acidic feedstock is adjusted to a value that is suitable for the enzymatic hydrolysis reaction. Typically, this involves the addition of alkali to a pH of between about 4 to about 6, which is the optimal pH range for cellulases, although the pH can be higher if alkalophilic cellulases are used.

In one type of pretreatment process, the pressure produced by the steam is brought down rapidly with explosive decompression, which is known as steam explosion. Foody, (U.S. Pat. No. 4,461,648) describes the equipment and conditions used in steam explosion pretreatment. Steam explosion with sulfuric acid added to achieve a pH of 0.4 to 2.0 has been the standard pretreatment process for two decades. It produces pretreated material that is uniform and requires less cellulase enzyme to hydrolyze cellulose than other pretreatment processes.

Cellulase enzymes catalyze the hydrolysis of the cellulose (β-1,4-D-glucan linkages) in the feedstock to products such as glucose, cellobiose, and other cellooligosaccharides. Cellulase is a generic term denoting a multienzyme mixture comprising exo-cellobiohydrolases (CBH), endoglucanases (EG) and β-glucosidases (βG) that can be produced by a number of plants and microorganisms. Cellulase enzymes work synergistically to hydrolyze cellulose to glucose. CBHI and CBHII generally act on the ends of the glucose polymers in cellulose microfibrils liberating cellobiose (Teeri and Koivula, *Carbohydr. Europe,* 1995, 12:28-33), while the endoglucanases act at random locations on the cellulose. Together, these enzymes hydrolyze cellulose to smaller cellooligosaccharides, primarily cellobiose. Cellobiose is hydrolyzed to glucose by β-glucosidase. It is known that most exo-cellobiohydrolases (CBH) and endoglucanases (EG) bind to cellulose in the feedstock via carbohydrate-binding modules (CBMs), such as cellulose-binding domains (CBDs), while most β-glucosidase enzymes, including *Trichoderma* and *Aspergillus* β-glucosidase enzymes, do not contain such binding modules and thus remain in solution. Cellulase enzymes may contain a linker region that connects the catalytic domain to the carbohydrate binding module. The linker region is believed to facilitate the activity of the catalytically active domain.

Cellulase enzymes containing a CBD have been produced by genetic engineering. For example, U.S. Pat. No. 5,763,254 (Wöldike et al.) discloses the production of genetically engineered cellulose degrading enzymes derived from *Humicola, Fusarium* and *Myceliopthora* containing carbohydrate-binding domains. The goal of the studies was to produce cellulose or hemicellulose-degrading enzymes with novel combinations of the catalytically active domain, the linker region and the CBD or to produce CBD-containing cellulose or hemicellulose-degrading enzymes from those that lack a CBD. However, the ability of these novel enzymes to hydrolyze lignocellulosic feedstock was not demonstrated.

One significant problem with enzymatic hydrolysis processes is the large amount of cellulase enzyme required, which increases the cost of the process. The cost of cellulase accounts for more than 50% of the cost of hydrolysis. There are several factors that contribute to the enzyme requirement, but one of particular significance is the presence of compounds that reduce the reaction rate of cellulases and/or microorganisms in the subsequent fermentation of the sugar. For example, glucose released during the process inhibits cellulases, particularly β-glucosidase (Alfani et al., *J. Membr. Sci.*, 1990, 52:339-350). Cellobiose produced during cellulose hydrolysis is a particularly potent inhibitor of cellulase (Tolan et al. in Biorefineries—Industrial Processes and Products, Vol. 1 Ed. Kamm et al., Chapter 9, page 203). Other soluble inhibitors are produced during pretreatment including sugar degradation products such as furfural and hydroxylmethyl furfural, furan derivatives, organic acids, such as acetic acid, and soluble phenolic compounds derived from lignin. These compounds also inhibit yeast, which decreases ethanol production and consequently makes the process more costly. Although the effects of inhibitors can be reduced by performing the hydrolysis at a more dilute concentration, this requires the use of a large hydrolysis reactor, which adds to the expense of the process.

Simultaneous Saccharification and Fermentation (SSF) is a method of converting lignocellulosic biomass to ethanol which minimizes glucose inhibition of cellulases (see for example Ghosh et al., *Enzyme Microb. Technol.*, 1982, 4:425-430). In an SSF system, enzymatic hydrolysis is carried out concurrently with yeast fermentation of glucose to ethanol. During SSF, the yeast removes glucose from the system by fermenting it to ethanol and this decreases inhibition of the cellulase. However, a disadvantage of this process is that the cellulase enzymes are inhibited by ethanol. In addition, SSF is typically carried out at temperatures of 35-38° C., which is lower than the 50° C. optimum for cellulase and higher than the 28° C. optimum for yeast. This intermediate temperature results in substandard performance by both the cellulase enzymes and the yeast. As a result, the hydrolysis requires very long reaction times and very large reaction vessels, both of which are costly.

Another approach that has been proposed to reduce inhibition by glucose, cellobiose, and other soluble inhibitors is removing hydrolysis products throughout hydrolysis by carrying out the reaction in a membrane reactor. A membrane reactor contains an ultrafiltration membrane which retains particles and high molecular weight components, such as enzyme, while allowing lower molecular weight molecules, such as sugars, to pass through the membrane as permeate.

An example of a process utilizing a membrane reactor is described in Ohlson and Trägårdh (*Biotech. Bioeng.*, 1984, 26:647-653). In this process, the enzymatic hydrolysis of pretreated sallow (a willow tree species) is carried out in a reactor with a membrane having a 10,000 molecular weight cut off. Cellulases have a molecular weight of 50,000 and are therefore retained by the membrane in the hydrolysis reactor, while sugars are removed and replaced with buffer solution from a feed container with fresh substrate added intermittently. The rate of hydrolysis, as well as the yield of the soluble sugars, is enhanced due to the removal of inhibitors. However, a disadvantage of such reactors is that the membranes required for a commercial hydrolysis system are extremely large and expensive. The membranes are also prone to fouling by suspended solids present in the reaction mixture.

Various groups have investigated the recovery and recycling of cellulase enzymes during enzymatic hydrolysis to reduce the amount of the enzyme necessary during the conversion process. In some cases, this has also involved the continuous removal of hydrolyzates from the reaction mixture to remove inhibitory compounds.

For example, Ishihara et al. (*Biotech. Bioeng.*, 1991, 37:948-954) disclose the recycling of cellulase enzymes during the hydrolysis of steamed hardwood and hardwood kraft pulp in a reactor. The process involves the removal of a cellulase reaction mixture from the reactor, followed by the removal of insoluble residue containing lignin from the mixture by filtering with suction. The cellulase enzymes that are in the filtrate are separated from hydrolysis products, such as glucose and cellobiose, by ultrafiltration and then returned to the hydrolysis reactor. As stated by the investigators, a disadvantage of this system is that the extra step of solids removal would be impractical in an industrial application due to the rise in the cost of raw material. In addition, most of the cellulases remain bound to the cellulose and are difficult to recover.

Larry et al. (*Appl. Microbiol. Biotechnol.*, 1986, 25:256-261) describe an approach for the re-use of cellulases which involves performing the hydrolysis in a column reactor containing cellulose (Solka Floc). The hydrolyzed sugars are continuously removed by percolating the column with a steady stream of buffer. According to the investigators, the removal of sugar products should reduce product inhibition and enhance hydrolysis efficiencies. However, inadequate hydrolysis is obtained since unbound β-glucosidase and endoglucanase elute from the column.

Knutsen and Davis (*Appl. Biochem. Biotech.*, 2002, 98-100:1161-1172) report a combined inclined sedimentation and ultrafiltration process for recovering cellulase enzymes during the hydrolysis of lignocellulosic biomass. The goal of the process is to remove larger lignocellulosic particles so a membrane filter used during a subsequent step of ultrafiltration does not become clogged. The process first involves treating lignocellulosic particles with cellulase enzymes and then feeding the resulting mixture into an inclined settler. Large lignocellulosic particles, including enzyme bound to the particles, are retained in the inclined settler, while smaller particles and soluble enzyme are carried out with the settler overflow. The overflow is then fed to a crossflow ultrafiltration unit to recover unbound cellulases, while allowing for the passage of sugars. After ultrafiltration, the recovered cellulases are added to the hydrolysis reactor. The lignocellulosic particles remaining in the inclined settler, along with the bound enzyme, are returned to the reactor along with the settler underflow. One disadvantage of this system is that the operation of such a system on the scale of a commercial hydrolysis reactor, which is likely to be about 70 feet tall and process thousands of gallons of slurry every hour, would be prohibitively difficult. A second disadvantage of this system is that the concentration of glucose and cellobiose in the reactor remains unchanged throughout the process so that a high level of inhibition still occurs. A further disadvantage of the process is that it requires an expensive ultrafiltration step to recover unbound cellulases.

Mores et al. (*Appl. Biochem. Biotech.*, 2001, 91-93:297-309) report a combined inclined sedimentation and ultrafiltration process similar to that described by Knutsen and Davis (supra). However, the process of Mores et al. involves an extra clarification step involving subjecting the settler overflow to microfiltration prior to ultrafiltration to reduce fouling of the ultrafiltration membrane. The process of Mores et al. would be subject to the same limitations as those described for Knutsen and Davis (supra).

U.S. Pat. No. 3,972,775 (Wilke et al.) discloses a process for recycling cellulase in which the hydrolysis products are separated into an aqueous sugar-containing phase and a solid phase containing unhydrolyzed spent solids after the hydrolysis is complete. The spent solids are washed with water to recover enzyme adsorbed on it and the resulting wash water containing the desorbed enzyme is fed to the hydrolysis reaction. The remaining spent solids can be used as a source of fuel for the system. However, the process of Wilke et al. incurs the cost of the additional water wash after the hydrolysis, which is significant due to the large amount of solid material and the fine particulate nature of the solids. In addition, the process does not result in the removal of inhibitors of cellulase enzymes present during the hydrolysis reaction since the separation of hydrolyzates is carried out after completion of the hydrolysis reaction.

Ramos et al. (*Enzyme Microb. Technol.*, 1993, 15:19-25) disclose a process in which steam-exploded eucalyptus chips are hydrolyzed using cellulase with removal of soluble sugars and the recycling of enzyme. The process involves stopping the reaction at selected incubation times and collecting the unhydrolyzed, enzyme-containing residue on a sintered glass filter. The enzyme-containing residue is washed with hydrolysis buffer to remove soluble sugars. The washed residue is then re-suspended in fresh hydrolysis buffer containing fresh β-glucosidase enzyme and incubated at 45° C. for subsequent hydrolysis. A problem with this process is that the repeated addition of fresh β-glucosidase after re-suspension would significantly increase the expense of the process.

Lee et al. (*Biotech. Bioeng.*, 1994, 45:328-336) examine the recycling of cellulase enzymes in a procedure involving over five successive rounds of hydrolysis. The process involves adding cellulase enzymes and β-glucosidase (Novozym® 188) to peroxide-treated birch and recovering the residual substrate by filtering after 12 hours of hydrolysis. Fresh substrate is then added to the recovered residual substrate to achieve a total substrate concentration of 2% and the resulting mixture is re-suspended in buffer containing β-glucosidase and the hydrolysis is allowed to continue. Cellulase recycling followed by hydrolysis is subsequently repeated three times. Also disclosed is a procedure for recycling cellulases present in the complete reaction mixture both before and after all the cellulose is hydrolyzed. Similar to Ramos et al., a limitation of this process is that β-glucosidase must be added to the reaction at each recycling step.

U.S. Pat. No. 5,962,289 (Kilburn et al.) discloses a three-step enzymatic hydrolysis. The first step of the process involves adding both endoglucanase and exoglucanase to a lignocellulosic material to be hydrolyzed to cellobiose. The second step involves adding this material to an Avicel® column to adsorb the endoglucanase and exoglucanase. In a third step, the eluent containing cellobiose is then applied to a second Avicel® column containing β-glucosidase immobilized via a CBD. The immobilized β-glucosidase hydrolyzes the cellobiose into glucose. One limitation of this method is that the production of glucose is carried out in three distinct process steps, which is highly complex and costly. A second limitation is that sending the slurry of partially-hydrolyzed lignocellulosic material through the column of Avicel® at a high flow rate typical of a commercial hydrolysis process is very difficult. In addition, the highly inhibitory effects of cellobiose are present during the cellulose hydrolysis.

At present, there is much difficulty in the art to operate an efficient enzymatic hydrolysis of cellulose. A key obstacle is overcoming the inhibitory effects of glucose and especially cellobiose to cellulase. The development of such a system remains a critical requirement for a process to convert cellulose to glucose.

SUMMARY OF THE INVENTION

The present invention relates to enzymes for the hydrolysis of cellulose and methods of using same. More specifically, the present invention relates to cellulase and β-glucosidase enzymes for the enzymatic hydrolysis of cellulose to produce a hydrolysis product comprising glucose from a pretreated lignocellulosic feedstock.

It is an object of the invention to provide an improved method for the treatment of lignocellulosic feedstocks.

According to the present invention, there is provided an enzyme composition for the enzymatic hydrolysis of cellulose to produce a hydrolysis product comprising glucose from a pretreated lignocellulosic feedstock, the enzyme composition comprising cellulase enzymes, one or more than one β-glucosidase enzyme and a binding agent for binding the β-glucosidase enzyme to the pretreated lignocellulosic feedstock, wherein the hydrolysis is carried out by:

(i) partially hydrolyzing an aqueous slurry of the pretreated lignocellulosic feedstock with the enzyme composition to produce a hydrolyzed slurry comprising glucose, glucose oligomers or a combination thereof, and unhydrolyzed fiber solids comprising cellulose and lignin;

(ii) separating the unhydrolyzed fiber solids from the hydrolyzed slurry to produce separated fiber solids, wherein the cellulase enzymes and the one or more than one β-glucosidase enzyme bind to the separated fiber solids;

(iii) re-suspending the separated fiber solids in an aqueous solution to produce a re-suspended slurry; and (iv) continuing the hydrolysis of the re-suspended slurry to produce the hydrolysis product comprising glucose.

The binding agent may be a carbohydrate-binding module operably linked to the one or more than one β-glucosidase enzyme. Preferably, the carbohydrate-binding module is a cellulose-binding domain.

The present invention also pertains to the enzyme composition as described above, wherein the cellulase enzymes are produced by *Aspergillus, Humicola, Trichoderma, Bacillus, Thermobifida*, or a combination thereof. Preferably, the cellulase enzymes are produced by *Trichoderma*.

The present invention also pertains to the enzyme composition as described above, wherein the cellulase enzymes comprise a cellobiohydrolase (CBH) selected from the group consisting of CBHI and CBHII cellulase enzymes, and combinations thereof, and an endoglucanase (EG) selected from the group consisting of EGI, EGII, EGIV, EGV and EGVI cellulase enzymes, and combinations thereof.

The present invention also pertains to the enzyme composition as described above, wherein, in the step of partially-hydrolyzing (step (i)), about 75% to about 100% (w/w) of the total cellulase enzymes present in the enzyme composition bind to fiber solids present in the aqueous slurry.

The present invention also pertains to the enzyme composition as described above, wherein the one or more than one β-glucosidase enzyme is produced by *Aspergillus, Humicola, Trichoderma, Bacillus, Thermobifida*, or a combination thereof. Preferably the β-glucosidase enzyme is produced by *Trichoderma* or *Aspergillus*. The β-glucosidase enzyme may be naturally occurring or a genetically modified fusion protein.

The present invention also pertains to the enzyme composition as described above, wherein about 75% to about 100% (w/w), or about 90% to about 100% (w/w), of the total β-glucosidase enzyme present in the enzyme composition comprises a cellulose-binding domain. The cellulose-binding domain may be a Family I cellulose-binding domain. Furthermore, the cellulose-binding domain may be a bacterial or fungal cellulose-binding domain. Optionally, the β-glucosidase enzyme comprises a linker, which operably links the cellulose-binding domain to the β-glucosidase enzyme.

According to the present invention, there is also provided a use of an enzyme composition for the enzymatic hydrolysis of cellulose to produce a hydrolysis product comprising glucose from a pretreated lignocellulosic feedstock, the enzyme composition comprising cellulase enzymes, one or more than one β-glucosidase enzyme and a binding agent for binding the β-glucosidase enzyme to the pretreated lignocellulosic feedstock, wherein the use of the enzyme composition comprises:

(i) partially hydrolyzing an aqueous slurry of the pretreated lignocellulosic feedstock with the enzyme composition to produce a hydrolyzed slurry comprising glucose, glucose oligomers or a combination thereof, and unhydrolyzed fiber solids comprising cellulose and lignin;

(ii) separating the unhydrolyzed fiber solids from the hydrolyzed slurry to produce separated fiber solids, wherein the cellulase enzymes and the one or more than one β-glucosidase enzyme bind to the separated fiber solids;

(iii) re-suspending the separated fiber solids in an aqueous solution to produce a re-suspended slurry; and (iv) continuing the hydrolysis of the re-suspended slurry to produce the hydrolysis product comprising glucose.

The binding agent may be a carbohydrate-binding module operably linked to the one or more than one β-glucosidase enzyme. Preferably, the carbohydrate-binding module is a cellulose-binding domain.

The present invention also pertains to the use of the enzyme composition as described above, wherein the cellulase enzymes are produced by *Aspergillus, Humicola, Trichoderma, Bacillus, Thermobifida*, or a combination thereof. Preferably, the cellulase enzymes are produced by *Trichoderma*.

The present invention also pertains to the use of the enzyme composition as described above, wherein the cellulase enzymes comprise a cellobiohydrolase (CBH) selected from the group consisting of CBHI and CBHII cellulase enzymes, and combinations thereof, and an endoglucanase (EG) selected from the group consisting of EGI, EGII, EGIV, EGV and EGVI cellulase enzymes, and combinations thereof.

The present invention also pertains to the use of the enzyme composition as described above, wherein between about 75% and about 100% (w/w) of the total cellulase enzymes present in the enzyme composition bind to fiber solids present in the aqueous slurry.

The present invention also pertains to the use of the enzyme composition as described above, wherein the β-glucosidase enzyme is produced by *Aspergillus, Humicola, Trichoderma, Bacillus, Thermobifida*, or a combination thereof. Preferably the β-glucosidase enzyme is produced by *Trichoderma* or *Aspergillus*. The β-glucosidase enzyme may be naturally occurring or a genetically modified fusion protein. The β-glucosidase enzyme may be native to the host, or may be native to another genus or species and inserted into the host to be expressed.

The present invention also pertains to the use of the enzyme composition as described above, wherein about 75% to about 100% (w/w), preferably about 90% to about 100% (w/w), of the total β-glucosidase enzyme present in the enzyme composition comprises a cellulose-binding domain. The cellulose-binding domain may be a Family I cellulose-binding domain. Furthermore, the cellulose-binding domain may be a bacterial or fungal cellulose-binding domain. Optionally, the β-glucosidase enzyme comprises a linker.

According to the present invention, there is also provided a process for the enzymatic hydrolysis of cellulose with an enzyme composition comprising cellulase enzymes, one or more than one β-glucosidase enzyme and a binding agent for binding the β-glucosidase enzyme to the pretreated lignocellulosic feedstock to produce a hydrolysis product comprising glucose from a pretreated lignocellulosic feedstock, the process comprising:

(i) partially hydrolyzing an aqueous slurry of the pretreated lignocellulosic feedstock with the enzyme composition to produce a hydrolyzed slurry comprising unhydrolyzed fiber solids comprising cellulose and lignin and an aqueous phase comprising glucose, glucose oligomers or a combination thereof;

(ii) separating the unhydrolyzed fiber solids from the aqueous phase to produce separated fiber solids, wherein the cellulase enzymes and the one or more than one β-glucosidase enzyme bind to the separated fiber solids;

(iii) re-suspending the separated solids in an aqueous solution to produce a re-suspended slurry; and (iv) continuing the hydrolysis of the re-suspended slurry to produce the hydrolysis product comprising glucose.

The binding agent may be a carbohydrate binding module operably linked to the one or more than one β-glucosidase enzyme. Preferably, the carbohydrate binding module is a cellulose-binding domain.

The pretreated lignocellulosic feedstock may be obtained from wheat straw, oat straw, barley straw, corn stover, soybean stover, canola straw, rice straw, sugar cane, bagasse, switch grass, reed canary grass, cord grass, or miscanthus.

The present invention also pertains to the process as described above, wherein, in the step of partially hydrolyzing (step (i)), the aqueous slurry has a suspended or undissolved solids content of about 3% to about 30% (w/w). This aqueous slurry may be concentrated prior to the step of partially-hydrolyzing (step (i)). Preferably, the aqueous slurry is prepared in water.

The present invention also pertains to the process as described above, wherein, in the step of partially-hydrolyzing (step (i)), the pH of the aqueous slurry is from about 4.5 to about 5.5, or between about 4.5 and 5.0. The temperature of the aqueous slurry may be between about 45° C. to about 55° C.

The present invention also pertains to the process as described above, wherein, in the step of partially-hydrolyzing (step (i)), the cellulase enzymes are added at a dosage of about 1.0 to about 40.0 IU per gram of cellulose. The cellulase enzymes may be produced by *Aspergillus, Humicola, Trichoderma, Bacillus, Thermobifida*, or a combination thereof. Preferably, between about 75% and 100% (w/w) of the total cellulase enzymes present bind to fiber solids present in the aqueous slurry.

The present invention also pertains to the composition, use of the composition, or process as described above, wherein, in the step of partially hydrolyzing (step (i)), the one or more than one β-glucosidase enzyme is added at a dosage of about 35 to about 200 IU per gram of cellulose. The β-glucosidase enzymes may be produced by *Aspergillus, Humicola, Trichoderma, Bacillus, Thermobifida*, or a combination thereof. Preferably, the β-glucosidase is produced by *Aspergillus* or *Trichoderma*. The β-glucosidase enzyme may be native to the host, or may be native to another genus or species and inserted into the host to be expressed.

The present invention also pertains to the process as described above, wherein the unhydrolyzed solids are separated by microfiltration, centrifugation, vacuum filtration or pressure filtration. Preferably, the unhydrolyzed solids are separated by microfiltration.

The step of continuing the hydrolysis of the re-suspended slurry may be carried out for about 12 to about 200 hours. Preferably, a stream comprising glucose produced in step (i) is combined with a stream comprising glucose produced in step (iv) to produce a combined sugar stream.

Preferably, about 70% to about 100% of cellulose in the aqueous slurry is converted to glucose.

During the step of re-suspending (step (iii)), the aqueous solution may be process water.

The present invention also pertains to the process as described above, wherein the process is carried out in a hydrolysis system which comprises a hydrolysis reactor selected from the group consisting of an agitated tank, an unmixed tank, an agitated tower and an unmixed tower. The agitated tower or the unmixed tower may be either a downflow tower or an upflow tower. The process may be a batch process or a continuous process.

The present invention overcomes several disadvantages of the prior art by taking into account the difficulties encountered in steps carried out during the conversion of lignocellulosic feedstock to glucose. By separating the hydrolyzed solids from the aqueous phase and re-suspending the separated solids with an aqueous solution, glucose, cellobiose, and other compounds present in the aqueous phase that inhibit the cellulase enzymes are removed or their concentrations are reduced. In the absence of glucose or cellobiose, or by decreasing their concentration, the hydrolysis can proceed with enhanced efficiency. By performing a hydrolysis of the aqueous feedstock slurry with cellulase enzymes and a β-glucosidase enzyme that binds to the pretreated feedstock, the β-glucosidase enzyme is carried through to the re-suspended slurry rather than being removed with the aqueous phase. Since β-glucosidase is present in the re-suspended slurry, when the hydrolysis is allowed to continue, any cellobiose remaining in the feedstock is efficiently converted to glucose. Furthermore, cellulase activity will be present when the hydrolysis is continued, as cellulase enzymes also bind to the pretreated feedstock and are carried through to the re-suspended slurry. A further advantage of the invention is that β-glucosidase enzyme does not need to be added during continued hydrolysis of the re-suspended slurry as would required if the enzyme remained in the aqueous phase, thereby making the process less costly.

This summary of the invention does not necessarily describe all features of the invention.

BRIEF DESCRIPTION OF THE DRAWINGS

These and other features of the invention will become more apparent from the following description in which reference is made to the appended drawings wherein:

In FIG. 2A, the cellulase dosage is 16 mg/g and in FIG. 2B, the cellulase dosage is 24 mg/g.

In FIG. 4A, the incubation was carried out at 4° C. and in FIG. 4B, the incubation was carried out at 50° C. After 30 minutes of incubation, the reaction mixtures were centrifuged and the supernatant fraction separated by SDS-PAGE and visualized by coomassie blue stain.

DETAILED DESCRIPTION

Figure 1A:
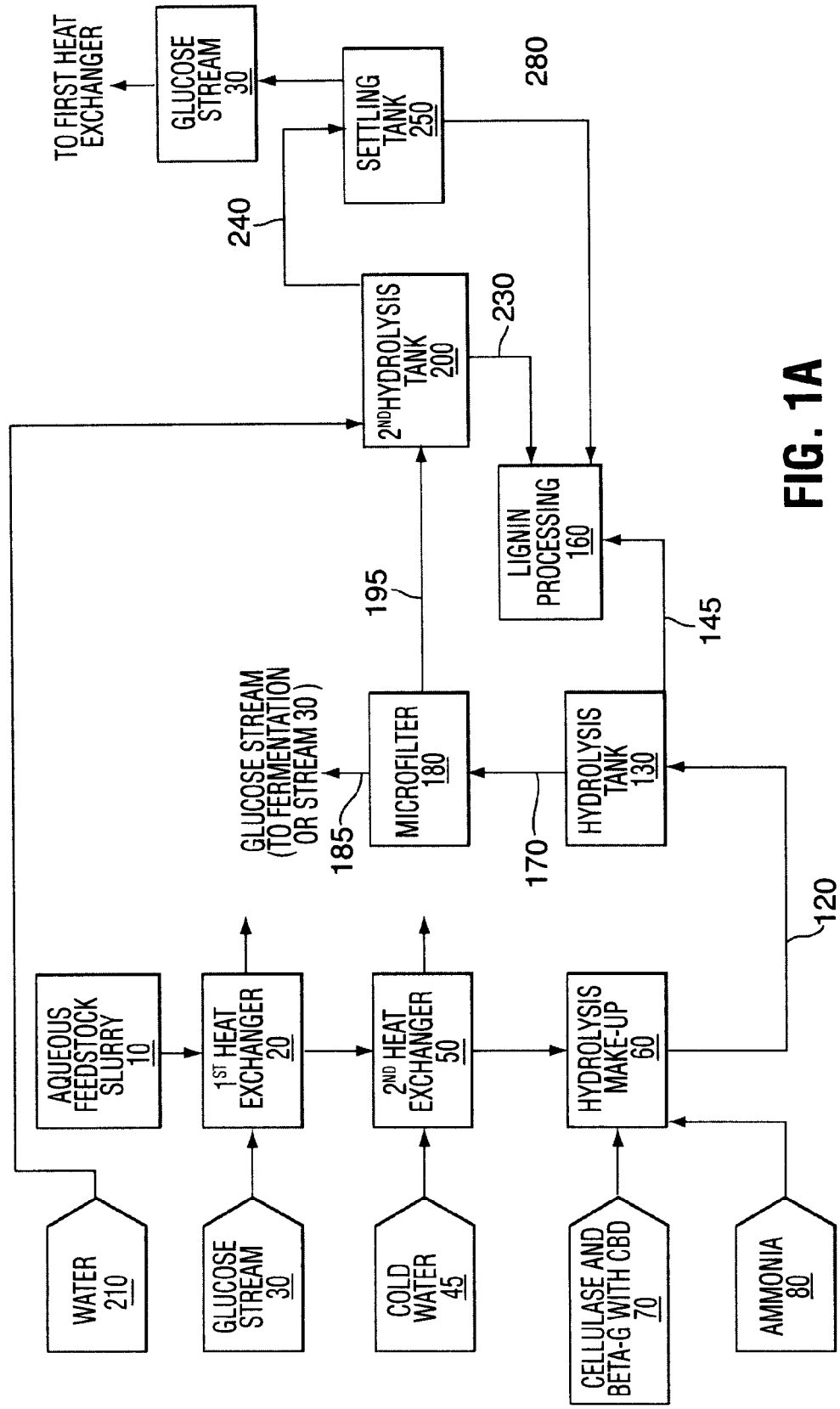
FIG. 1A shows a process flow diagram illustrating the steps of processing a lignocellulosic feedstock according to embodiments of the invention.

The following description is of preferred embodiments.

The present invention relates to enzymes for the improved hydrolysis of cellulose. More specifically, the present invention relates to cellulases and β-glucosidase enzymes for the improved enzymatic conversion of lignocellulosic feedstocks and methods of using same.

The following description is of an embodiment by way of example only and without limitation to the combination of features necessary for carrying the invention into effect.

The invention provides an enzyme composition and process for the hydrolysis of lignocellulosic feedstocks which improves the economics of enzymatic hydrolysis by decreasing inhibition by glucose and other compounds. The process involves performing a partial hydrolysis of a pretreated feedstock slurry with cellulases and one or more than one β-glucosidase that bind to the pretreated feedstock via a binding agent, and then separating unhydrolyzed fiber solids, which contain lignin and unhydrolyzed cellulose, from the aqueous phase, which contains glucose, glucose oligomers and cellobiose. The separated solids are then re-suspended in an aqueous solution to produce a re-suspended slurry. The cellulases and β-glucosidase enzyme are carried through to the re-suspended slurry by virtue of their ability to bind to the solids. The hydrolysis of the re-suspended slurry is then allowed to continue to produce a hydrolysis product comprising glucose. By separating the solids phase and aqueous phase, glucose and other soluble inhibitors, such as cellobiose, are removed or their concentrations are reduced so that the hydrolysis can continue without, or with reduced, inhibition.

The process may be a continuous process, with continuous feeding of pretreated feedstock slurry and withdrawal of hydrolysis product. Alternately, the process may be a batch process.

The process is carried out on a pretreated feedstock slurry so that the digestibility of the cellulose in the feedstock by the cellulase enzymes is enhanced. The cellulase enzymes convert at least a portion of the cellulose in the feedstock to glucose, cellobiose, glucose oligomers, or a combination thereof.

The feedstock for the process is a lignocellulosic material. By the term "lignocellulosic feedstock", it is meant any type of plant biomass such as, but not limited to, non-woody plant biomass, cultivated crops such as, but not limited to grasses, for example, but not limited to, C4 grasses, such as switch grass, cord grass, rye grass, miscanthus, reed canary grass, or a combination thereof, sugar processing residues, for example, but not limited to, baggase, beet pulp, or a combination thereof, agricultural residues, for example, but not limited to, soybean stover, corn stover, rice straw, rice hulls, barley straw, corn cobs, wheat straw, canola straw, oat straw, oat hulls, corn fiber, or a combination thereof, forestry biomass for example, but not limited to, recycled wood pulp fiber, sawdust, hardwood, for example aspen wood softwood, or a combination thereof. Furthermore, the lignocellulosic feedstock may comprise cellulosic waste material or forestry waste materials such as, but not limited to, newsprint, cardboard and the like. Lignocellulosic feedstock may comprise one species of fiber or, alternatively, lignocellulosic feedstock may comprise a mixture of fibers that originate from different lignocellulosic feedstocks. In addition, the lignocellulosic feedstock may comprise fresh lignocellulosic feedstock, partially dried lignocellulosic feedstock, fully dried lignocellulosic feedstock, or a combination thereof.

Lignocellulosic feedstocks comprise cellulose in an amount greater than about 20%, more preferably greater than about 30%, more preferably greater than about 40% (w/w). For example, the lignocellulosic material may comprise from about 20% to about 50% (w/w) cellulose, or more, or any amount therebetween, for example, but not limited to 20, 22, 24, 26, 28, 30, 32, 34, 36, 38, 40, 42, 44, 46, 48 and 50% (w/w) cellulose. The lignocellulosic feedstock also comprises lignin in an amount greater than about 10%, more preferably in an amount greater than about 15% (w/w). The lignocellulosic feedstock may also comprise small amounts of sucrose, fructose and starch.

Examples of preferred lignocellulosic feedstocks include (1) agricultural wastes such as corn stover, wheat straw, barley straw, canola straw, oat straw, rice straw and soybean stover; and (2) grasses such as switch grass, miscanthus, cord grass and reed canary grass.

The present invention is practiced with lignocellulosic material that has been pretreated. Pretreatment methods are intended to deliver a sufficient combination of mechanical and chemical action so as to disrupt the fiber structure and increase the surface area of feedstock accessible to cellulase enzymes. Mechanical action typically includes, but is not limited to, the use of pressure, grinding, milling, agitation, shredding, compression/expansion, or other types of mechanical action. Chemical action can include, but is not limited to, the use of heat (often steam), acid, alkali and solvents. Several chemical and mechanical pretreatment methods are well known in the art.

Prior to pretreatment, the lignocellulosic feedstock may be leached. This may be carried out, for example, as disclosed in WO 02/070753 (Griffin et al., which is incorporated herein by reference). However, even if leaching is practiced, a substantial amount of inhibiting compound is produced in the subsequent pretreatment process.

The pretreatment is employed to increase the susceptibility of the lignocellulosic feedstock slurry to hydrolysis by cellulase enzymes. For example, the pretreatment may be carried out to hydrolyze the hemicellulose, or a portion thereof, that is present in the lignocellulosic feedstock to monomeric sugars, for example xylose, arabinose, mannose, galactose, or a combination thereof. Preferably, the pretreatment is performed so that nearly complete hydrolysis of the hemicellulose and a small amount of conversion of cellulose to glucose occurs. The cellulose is hydrolyzed to glucose in a subsequent step that uses cellulase enzymes. During the pretreatment, typically a dilute acid, at a concentration from about 0.02% (w/v) to about 2% (w/v), or any amount therebetween (measured as the percentage weight of pure acid in the total weight of dry feedstock plus aqueous solution) is used for the pretreatment of the lignocellulosic feedstock. Preferably, the pretreatment is carried out at a temperature of about 180° C. to about 250° C. for a time of about 6 seconds to about 120 seconds, at a pH of about 0.8 to about 2.0. Pretreatment may be carried out in a single stage or in more than one stage. Preferably, at least one stage is carried out at the temperature range, for the time period and the pH range set out above.

One approach to the pretreatment of the feedstock is steam explosion, using the process conditions described in U.S. Pat. Nos. 4,461,648 and 4,237,226 (which are herein incorporated by reference). Another method of pretreating the feedstock slurry involves continuous pretreatment, meaning that the lignocellulosic feedstock is pumped through a reactor continuously. Continuous acid pretreatment is familiar to those skilled in the art, see, for example, U.S. Pat. No. 5,536,325 (Brink); co-pending U.S. application No. 60/687,224 (Foody and Tolan); U.S. Pat. No. 4,237,226 (Grethlein; which are incorporated herein by reference). Other methods that are known in the art may be used as required for the preparation of a pretreated feedstock, for example, but not limited to, those disclosed in U.S. Pat. No. 4,556,430 (Converse et al.; which is incorporated herein by reference).

The pretreated lignocellulosic feedstock may optionally be washed with water prior to enzymatic hydrolysis. The washing or leaching step can remove some of the inhibitors of cellulase enzymes and yeast, such as dissolved sugars and sugar degradation products, dissolved lignin and phenolic compounds and other organic compounds in the system. However, although washing after pretreatment falls within the scope of the invention, it may not result in the removal of all of the insoluble impurities present and it increases the cost of the process.

The pretreated lignocellulosic material is slurried in an aqueous solution to produce an aqueous feedstock slurry or "aqueous slurry". For example, but without wishing to be limiting, the aqueous solution may be process water, fresh water, steam condensate or process recycle streams. The concentration of pretreated lignocellulosic feedstock in the aqueous slurry depends on the particle size, water retention, pump capacity and other properties of the feedstock. Typically, the concentration is between about 3% and 30% (w/w), or between about 10% and about 20% (w/w) fiber solids (also known as suspended or undissolved solids), or any amount therebetween. The aqueous slurry preferably has a solids concentration that enables it to be pumped. As is well known in the art, the concentration of suspended or undissolved solids can be determined by filtering a sample of the slurry using glass microfiber filter paper, washing the filter cake with water, and drying the cake overnight at 105° C. It is preferred that the fiber solids comprise at least about 20% to about 70% cellulose by weight, or any amount therebetween. For example, the suspended solids may comprise 30%, 35%, 40%, 45%, 50%, 55%, 60%, 65% or 70% cellulose by weight.

The pH of the aqueous slurry is generally adjusted to within the range of the optimum pH for the cellulase enzymes used. Generally, the pH of the aqueous slurry is adjusted to within a range of about 3.0 to about 7.0, or any pH therebetween. Typically, the pH is within a range of about 4.5 to about 5.5, or any pH therebetween. However, it should be appreciated that the pH of the slurry can be higher or lower than about 4.5 to about 5.5 if the cellulase enzymes used are alkalophilic or acidophilic. The pH of the slurry may be adjusted using any suitable acid or base known in the art. For example, if the slurry is basic (e.g., if a basic pretreatment is performed), sulfuric acid may be used. If the slurry is acidic, the pH may be adjusted with bases selected from the group consisting of ammonia, ammonium hydroxide, lime, calcium hydroxide, potassium hydroxide, magnesium hydroxide, sodium hydroxide and a mixture thereof. Preferably, the base is selected from the group consisting of ammonia, ammonium hydroxide and sodium hydroxide.

The temperature of the aqueous feedstock slurry is adjusted so that it is within the optimum range for the activity of the cellulase enzymes. Generally, a temperature of about 45° C. to about 55° C., or any temperature therebetween, is suitable for most cellulase enzymes. However, the temperature of the slurry may be higher for thermophilic cellulase enzymes.

The cellulase enzymes and a β-glucosidase enzyme with binding agent are added to the aqueous slurry, prior to, during, or after the adjustment of the temperature and pH of the aqueous slurry after pretreatment. Preferably the cellulase enzymes and the β-glucosidase enzyme are added to the pretreated lignocellulosic feedstock slurry after the adjustment of the temperature and pH of the slurry. The partial hydrolysis of the pretreated lignocellulosic material is then carried out.

A cellulase is an enzyme with hydrolytic activity toward cellulose in the fiber solids and that comprises at least one catalytic domain. A cellulase enzyme generally has additional domains, including, but not limited to, a carbohydrate-binding module or other functional domains.

By the term "cellulase enzymes" or "cellulases," it is meant a mixture of enzymes that hydrolyze cellulose. The mixture may include glucobiohydrolases (GBH), cellobiohydrolases (CBH) and endoglucanases (EG). Although GBH enzymes may form a component of the enzyme mixture, their use in the enzymatic hydrolysis of cellulose is less common than CBH and EG enzymes. In a non-limiting example, the mixture includes CBH and EG enzymes. The GBH enzyme primarily hydrolyzes cellulose polymer chains from their ends to release glucose, while the CBH enzyme primarily hydrolyzes cellulose polymer chains from their ends to release cellobiose and the EG enzyme primarily hydrolyzes cellulose polymer in the middle of the chain. The GBH enzyme may be an enzyme having an activity of type EC#3.2.1.73, the CBH enzyme may have an enzyme activity of type EC#3.2.1.91 and the EG enzyme may have an activity of type EC#3.2.1.4 or EC#3.2.1.151.

The cellulase enzymes can be produced by a number of plants and microorganisms. The process of the present invention can be carried out with any type of cellulase enzymes, regardless of their source. Among the most widely studied, characterized and commercially produced cellulases are those obtained from fungi of the genera *Aspergillus, Humicola*, and *Trichoderma*, and from the bacteria of the genera *Bacillus* and *Thermobifida*. Cellulase produced by the filamentous fungi *Trichoderma longibrachiatum* comprises at least two cellobiohydrolase enzymes termed CBHI and CBHII and at least four EG enzymes. As well, EGI, EGII, EGIII, EG V and EGVI cellulases have been isolated from *Humicola insolens* (see Schulein et al., *Proceedings of the Second TRICEL Symposium on Trichoderma reesei* Cellulases and Other Hydrolases, Espoo 1993, P. Suominen and T. Reinikainen, Eds. Foundation for Biotechnical and Industrial Fermentation Research, Helsinki 8:109-116, which is incorporated herein by reference).

The CBHI enzyme is defined as a CBH that primarily hydrolyzes cellulose polymer chains by a retaining mechanism as would be known to one of skill in the art. The CBHI enzyme may be processive. The CBHI enzyme may be a member of a Family 7, 10 or Family 48 glycohydrolases. In a preferred embodiment, the CBHI enzyme is a member of Family 7. In a more preferred embodiment, the CBHI enzyme is the Family 7 CBHI from *Trichoderma*.

The CBHII enzyme is defined as an enzyme that primarily hydrolyzes cellulose polymer chains by an inverting mechanism as would be known to one of skill in the art. The CBHII enzyme may be processive. The CBHII enzyme may be a member of Family 6, 9 or 74. In a preferred embodiment, the CBHII enzyme is a member of Family 6. In a more preferred embodiment, the CBHII enzyme is the Family 6 CBHII from *Trichoderma*.

Examples of EG enzymes that may be used in the practice of this invention are set out in Table 1 below:

TABLE 1

Examples of EG enzymes

| EG enzyme | Glucohydrolase Family |
|---|---|
| EGI | 7 |
| EGII | 5 |
| EGIII | 12 |
| EGIV | 61 |
| EGV | 45 |
| EGVI | 74 |

Preferably, the EG enzymes are fungal enzymes, such as enzymes expressed from *Trichoderma*. The EG enzymes preferably contain a CBD (cellulose binding domain), although a certain proportion of the EG enzymes may be included in the cellulase enzyme mixture that lack a CBD.

The cellulase enzyme dosage is chosen to convert the cellulose of the pretreated feedstock to glucose. For example, an appropriate cellulase dosage can be about 1.0 to about 40.0 Filter Paper Units (FPU or IU) per gram of cellulose, or any amount therebetween. The FPU is a standard measurement familiar to those skilled in the art and is defined and measured according to Ghose (*Pure and Appl. Chem.*, 1987, 59:257-268).

Cellulase enzymes used in the practice of this invention bind to components of the pretreated feedstock. However, it should be apparent that the enzyme composition may comprise some cellulases that do not bind to the pretreated lignocellulosic feedstock, such as those that do not comprise a cellulose-binding domain. The percentage of cellulase enzymes that bind to cellulose (solids) may be between about 75% and 100% (w/w) of the total cellulase enzymes present in the enzyme composition; for example, the percentage of cellulase enzymes that bind to cellulose may be about 75, 78, 80, 83, 85, 87, 90, 93, 95, 97, or 100% (w/w) of the total cellulase enzymes present in the enzyme composition.

The conversion of cellobiose to glucose is carried out by the β-glucosidase. By the term "β-glucosidase", it is meant any enzyme that hydrolyzes the glucose dimer, cellobiose, to glucose. The activity of the β-glucosidase enzyme is defined by its activity by the Enzyme Commission as EC#3.2.1.21. The β-glucosidase enzymes for use in this invention are water soluble. There are many microbes that make β-glucosidase and the properties of these enzymes vary, including structure (molecular weight, three-dimensional orientation, amino acid composition and active site) and catalytic activity (rate and kinetics of cellobiose hydrolysis and ability to act on other substrates). The β-glucosidase enzyme may come from various sources; however, in all cases, the β-glucosidase enzyme is capable of hydrolyzing cellobiose to glucose. The β-glucosidase enzyme may be a Family 1 or Family 3 glycoside hydrolase, although other family members may be used in the practice of this invention. The preferred β-glucosidase enzyme for use in this invention is the Bgl1 protein from *Trichoderma reesei*. Other forms might include other Bgl proteins from *Trichoderma* or β-glucosidase enzymes from other organisms.

The binding of the β-glucosidase to the pretreated feedstock is effected by a binding agent that binds the β-glucosidase enzyme to the pretreated lignocellulosic feedstock. By the term "binding agent", it is meant any chemical compound for binding the β-glucosidase to the fiber solids. The affinity of the binding agent for the pretreated feedstock is strong enough to allow the β-glucosidase enzyme to adhere to the fiber solids in the aqueous feedstock slurry, thereby allowing it to be carried through to the second hydrolysis (continued hydrolysis).

The binding agent may be a chemical attached to the β-glucosidase enzyme in the form of a chemical modification. This modification involves attaching to the enzyme a chemical with sufficient affinity for the fiber solids. Examples of suitable chemicals include detergents, surfactants, polyglycols, proteins and protein fragments. Examples of detergents and surfactants include, but are not limited to, bile acids (cholate, deoxycholate, taurocholate, glycocholate, and glycodeoxycholate are examples), alkyl glycosides (n-nonyl-β-D-glucopyranoside, n-octyl-β-D-glucopyranoside, n-heptyl-β-D-glucopyranoside, n-hexyl-β-D-glucopyranoside, dodecyl-β-D-maltoside octyl-β-D-thioglucopyranoside, glucopyranoside, and decyl-β-D-maltoside are examples) and zwittergents. Examples of polyglycols include, but are not limited to, polyethylene glycol and polyoxyethylenes.

The binding agent may also be a protein or protein fragment. Examples of proteins and protein fragments include those described above for use as binding domains. Further examples of proteins that can serve as a binding agent include, but are not limited to, hydrophobin, streptolysin, swollenin or expansin. Examples of protein fragments that can serve as binding agents include, but are not limited to, polytryptophan, polytyrosin and amphipathic helices.

Preferably, the binding agent is a binding domain such as a carbohydrate-binding module (CBM) that is operably linked to the β-glucosidase enzyme. By the term "carbohydrate-binding module" or "CBM", it is meant any protein or peptide sequence that non-covalently binds to carbohydrate(s) present in the fiber solids. Preferably, the carbohydrate-binding module is a cellulose-binding domain (CBD) that binds to cellulose in the fiber solids.

CBDs are found in nature as discrete domains in proteins such as cellulases and also in non-hydrolytic enzymes. To date, over twenty-five families of CBD sequences have been identified. The CBD for the practice of this invention may be derived from any source of CBDs. For example, the CBD may be derived from a bacteria or fungus, although CBDs have been isolated from a variety of other organisms. Non-limiting examples of microbes that the CBD may be derived from include *Aspergillus, Humicola, Trichoderma, Bacillus, Thermobifida*, or a combination thereof. Preferred CBD sequences for the practice of the invention are Type I CBDs, which are derived from fungi. Alternatively, the DNA sequence encoding a CBD may be prepared synthetically by methods known to those of skill in the art such as the phosphoramidite method (Beaucage and Caruthers, *Tetrahedron Letters,* 1981, 22:1859-1869, which is incorporated herein by reference).

The term "operably linked" refers to a linkage between the β-glucosidase enzyme and the binding domain which enables the binding domain to adhere to the fiber solids in the aqueous slurry. The linkage may be via a linker or the binding domain may be linked to the β-glucosidase without an intervening linker region.

A further example of a binding agent that may be used in the practice of the invention is a chemical that associates with both the β-glucosidase enzyme and the fiber solids. Non-limiting examples of such chemicals include, but are not limited to, polycations, polyanions, flocculents and amphipathic molecules. Furthermore, this chemical may be a protein or protein fragment, such as those described above for use as binding domains, or a chemical such as those described above for use in chemical modification.

By the term "linker", it is meant an amino acid sequence adjoining the cellulose-binding domain of a cellulase or β-glucosidase enzyme and connecting it to the catalytically active domain of the enzyme. The linker region may be hydrophilic and uncharged and enriched in certain amino acids, including glycine, asparagine, proline, serine, threonine, glutamine, or combinations thereof. Preferably, the structure of the linker imparts flexibility to the sequence. While not wishing to be bound by theory, the flexible structure is believed to facilitate the activity of the catalytic domain. However, as would be evident to one of skill in the art, it is not essential that a linker is present.

The ability of a β-glucosidase enzyme or a cellulase enzyme to bind to cellulose may be determined by cellulose-binding assays using pretreated lignocellulosic material. Such assays are familiar to those skilled in the art and involve contacting 5 grams of pretreated lignocellulosic material with 50 mg β-glucosidase enzyme, with binding agent, in an aqueous solution for 5 to 15 minutes at a temperature of 20° C. to 40° C., then separating the fiber solids from the enzyme by filtration and measuring the amount of enzyme remaining in solution. The binding agent binds to the β-glucosidase and the fiber solids, thereby allowing the β-glucosidase enzyme to be retained in the hydrolysis reactor along with the fiber solids.

Any source of β-glucosidase may be used in the practice of the invention. For example, the β-glucosidase enzyme may be derived from *Aspergillus, Humicola, Trichoderma, Bacillus, Thermobifida*, or a combination thereof. Preferably, the β-glucosidase enzyme is derived from *Trichoderma* or *Aspergillus*. The β-glucosidase enzyme derived from *Trichoderma* is of molecular weight 74,000 (as measured by SDS-polyacrylamide gel electrophoresis) and has an isoelectric point of 8.3 (as measured by non-denaturing isoelectric focusing polyacrylamide gel electrophoresis). The β-glucosidase enzyme may be native to the host, or may be native to another genus or species and inserted into the host in which it is to be expressed.

The β-glucosidase containing a CBM, such as a CBD, may be a fusion protein produced by a genetic construct comprising a promoter sequence, a sequence encoding β-glucosidase and a sequence encoding a CBM. The genetic construct is expressed in a suitable expression system, for example, a bacterial of fungal expression system such as *Aspergillus, Humicola, Trichoderma, Bacillus, Thermobifida*, or a combination thereof. In addition, naturally occurring β-glucosidase enzymes with a CBM may be used in the practice of the invention. Naturally occurring β-glucosidase enzymes may be isolated from *Aspergillus, Humicola, Trichoderma, Bacillus, Thermobifida*, or a combination thereof. For example, a naturally occurring CBD-containing β-glucosidase has been purified and characterized from the white-rot fungus *Phanaerochaete chrysosporium* (Lymar et al., *Appl. Environ. Micro.,* 1995, 61: 2976-2980, the contents of which are incorporated herein by reference).

The dosage level of the β-glucosidase which is added to the aqueous slurry may be about 5 to about 400 β-glucosidase units per gram of cellulose, or any amount therebetween, or from about 35 to about 200 β-glucosidase units per gram of cellulose, or any amount therebetween. The β-glucosidase unit is measured according to the method of Ghose (supra).

It is preferred that the concentration of β-glucosidase present is high enough to ensure that cellobiose does not accumulate during the hydrolysis and inhibit the action of cellulase. It will be understood by those of skill in the art that *Trichoderma*, and other cellulase-producing microbes, usually produce only limited amounts of β-glucosidase. The methods set forth in White and Hindle, U.S. Pat. No. 6,015, 703 (which is incorporated herein by reference) may be employed to achieve enhanced levels of production of β-glucosidase by *Trichoderma*. Alternately, β-glucosidase may be produced in a separate *Aspergillus* fermentation and added to the cellulase mixture.

It should be appreciated that not all of the β-glucosidase in the enzyme composition may bind to the solids. For example, the amount of β-glucosidase enzyme present in the enzyme composition that comprises a CBD may be about 75% to about 100% (w/w), or any range therebetween, or about 85% to about 100% (w/w), or any range therebetween, or about 90% to about 100% (w/w), or any range therebetween, of the total β-glucosidase present. For example, the amount of β-glucosidase comprising a CBD in relation to the total amount of β-glucosidase present in the enzyme composition may be about 75, 78, 80, 83, 85, 87, 90, 93, 95, 97, or 100% (w/w).

The cellulase enzymes and β-glucosidase enzymes may be handled in an aqueous solution, or as a powder or granulate. The enzymes may be added to the aqueous slurry at any point prior to its introduction into a hydrolysis reactor. Alternatively, the enzymes may be added directly to the hydrolysis reactor, although addition of enzymes prior to their introduction into the hydrolysis reactor is preferred for optimal mixing. The enzymes may be mixed into the aqueous slurry using mixing equipment that is familiar to those of skill in the art.

FIG. 1A is a non-limiting example of how the cellulase hydrolysis may be carried out on a lignocellulosic feedstock pretreated as described above. Prior to cellulase hydrolysis, the aqueous feedstock slurry 10 is cooled. This may be carried out using a first heat exchanger 20 that exchanges against glucose product stream 30 or other suitable fluid. The aqueous slurry 10 may then be further cooled using a second fluid, for example, cold water 45, at second heat exchanger 50. The slurry 10 may then be pumped into a hydrolysis make-up tank 60, along with cellulase enzymes and a β-glucosidase enzyme 70 having a cellulose-binding domain, and ammonia 80 to adjust the pH. In this example, the contents of the hydrolysis make-up tank 60 are mixed and pumped out of the make-up tank 60, along pipe 120, to a hydrolysis tank 130. The make-up tank 60 may be used for adjusting the pH and achieving the desired temperature of the slurry.

It will be apparent to those of skill in the art that the enzymes may be mixed with the pretreated lignocellulosic feedstock slurry elsewhere, for example, within a line that feeds the make-up tank 60, including, but not limited to, upstream of first heat exchanger 20, a point between the first 20 and second heat exchanger 50, or a point just prior to entry of the feedstock to the make-up tank 60. The enzymes may also be added to the pretreated lignocellulosic feedstock slurry 10 after it exits the make-up tank 60; for example, they may be added to pipe 120.

After addition of the enzymes, the pretreated lignocellulosic feedstock is subjected to partial hydrolysis. By the term "partially hydrolyzing", it is meant hydrolyzing the pretreated lignocellulosic feedstock slurry so that complete conversion of the feedstock to glucose does not occur. The hydrolysis is carried out so that a portion of the cellulose in the aqueous slurry remains unconverted. This remaining cellulose is converted to cellobiose, glucose oligomers, glucose, or a combination thereof, during a step of further hydrolysis described in more detail below. The hydrolysis may result in about 30% to about 80% (w/w), or about 30% to about 60% (w/w) of the cellulose being converted to glucose; for example, 30, 33, 35, 38, 40, 43, 45, 50, 53, 55, 58, 60, 70 or 80% (w/w) of the cellulose may be converted to glucose. The partial hydrolysis of the lignocellulosic material may be allowed to continue for about 12 to about 24 hours, or any amount of time therebetween. For example, the reaction time could be about 12, 13, 14, 15, 16, 17, 18, 19, 20, 21, 22, 23 or 24 hours, or any time therebetween.

After the partial hydrolysis is carried out, unhydrolyzed fiber solids comprising cellulose and other insoluble components make up a solids phase of the partially-hydrolyzed slurry. The insoluble components, in addition to cellulose, that may be present in the solids phase include unconverted solids that are not digested by the cellulase enzymes, as well as non-lignocellulosic components, or other materials that are inert to cellulase, such as lignin and silica compounds. It should also be appreciated that the solids phase may comprise liquor. The solids phase may have a moisture content of 40-80%; for example, the solids phase may have a moisture content of 40, 45, 50, 55, 60, 65, 70, 75 or 80%.

The aqueous phase of the partially-hydrolyzed slurry contains glucose which inhibits cellulase enzymes. Additional soluble components that may be present in the aqueous phase include glucose oligomers, sugar degradation products such as furfural and hydroxylmethyl furfural, organic acids such as acetic acid, and phenolic compounds derived from lignin.

By the term "hydrolysis reactor", it is meant a reaction vessel used to carry out hydrolysis of the pretreated lignocellulosic feedstock slurry by the cellulase and β-glucosidase enzymes. The hydrolysis reactor must be of appropriate construction to accommodate the hydrolysis. The hydrolysis reactor may be jacketed with steam, hot water, or other heat source, to maintain the desired temperature. The hydrolysis reactor may be a tower with a height to diameter ratio of greater than 2:1, or a tank with a height to diameter ratio of less than 2:1.

The hydrolysis may be carried out in a hydrolysis reactor that is part of a hydrolysis system that comprises one or more than one hydrolysis reactor. The term "hydrolysis system" encompasses hydrolysis reactors as well as feed tanks, pumps, and other ancillary equipment. The choice of the number of hydrolysis reactors in the hydrolysis system depends on the cost of hydrolysis reactors, the volume of the aqueous slurry, and other factors. For a commercial-scale ethanol plant, the typical number of hydrolysis reactors is 4 to 12.

The hydrolysis may be carried out in a "solids-retaining hydrolysis reactor". The term "solids-retaining hydrolysis reactor", as used herein, refers to a hydrolysis reactor that retains fiber solids longer than the aqueous phase of the aqueous slurry to increase the reaction time of the cellulase and β-glucosidase enzymes with cellulose. A solids-retaining hydrolysis reactor may be an unmixed hydrolysis reactor in the sense that no mechanical agitation of the reactor contents is carried out during the hydrolysis reaction. An example of an unmixed hydrolysis reactor suitable for the practice of the invention is an upflow reactor which is described in WO 2006/063467 (Foody et al.), which is incorporated herein by reference. The solids-retaining hydrolysis reactor may also be a mixed reactor, in which case mechanical agitation of the reactor contents is carried out during the hydrolysis reaction. The active mixing within the hydrolysis tanks may be achieved by impellers or pumps as is well known in the art.

If the solids-retaining hydrolysis reactor is a tower, it may be an upflow tower in which the aqueous slurry and enzymes enter the tower directly at the bottom of the tower and are pumped upward through the tower. Alternatively, the tower may be a downflow tower in which the aqueous slurry is pumped downward through the tower. The upflow or downflow towers may be unmixed. Alternatively, there may be mixing at discreet levels.

Referring now to FIG. 1A, in a non-limiting example, the hydrolyzed slurry comprising glucose and unhydrolyzed fiber solids is removed from the top of the hydrolysis reactor 130 via line 170 and introduced to a microfiltration unit 180. The microfiltration unit 180 separates the fiber solids comprising cellulose from the aqueous phase of the hydrolyzed slurry. It should also be appreciated by those of skill in the art that the fiber solids comprise entrapped liquor. These separated fiber solids (line 195) are then re-suspended in a second hydrolysis reactor 200 and the hydrolysis is allowed to continue.

As described previously, during the hydrolysis, cellulases are bound to cellulose in the pretreated lignocellulosic feedstock. The β-glucosidase enzyme, which binds to the pretreated lignocellulosic feedstock, will also be bound to the fiber solids. Thus, when the fiber solids are separated from the aqueous phase of the slurry, not only will exo-cellobiohydrolases (CBH) and endoglucanases (EG) remain with the fiber solids phase, but also β-glucosidase.

A number of methods could be employed to separate the unhydrolyzed fiber solids from the aqueous phase. These can include methods that completely or almost completely separate the fiber solids from the aqueous phase, and methods that only partially separate the fiber solids from the aqueous phase. For example, the fiber solids may be separated from the aqueous phase by membrane filtration, centrifugation, or vacuum or pressure filtration. A preferred method of membrane filtration is microfiltration and a preferred method of centrifugation involves pumping the slurry through a hydroclone.

Figure 1B:
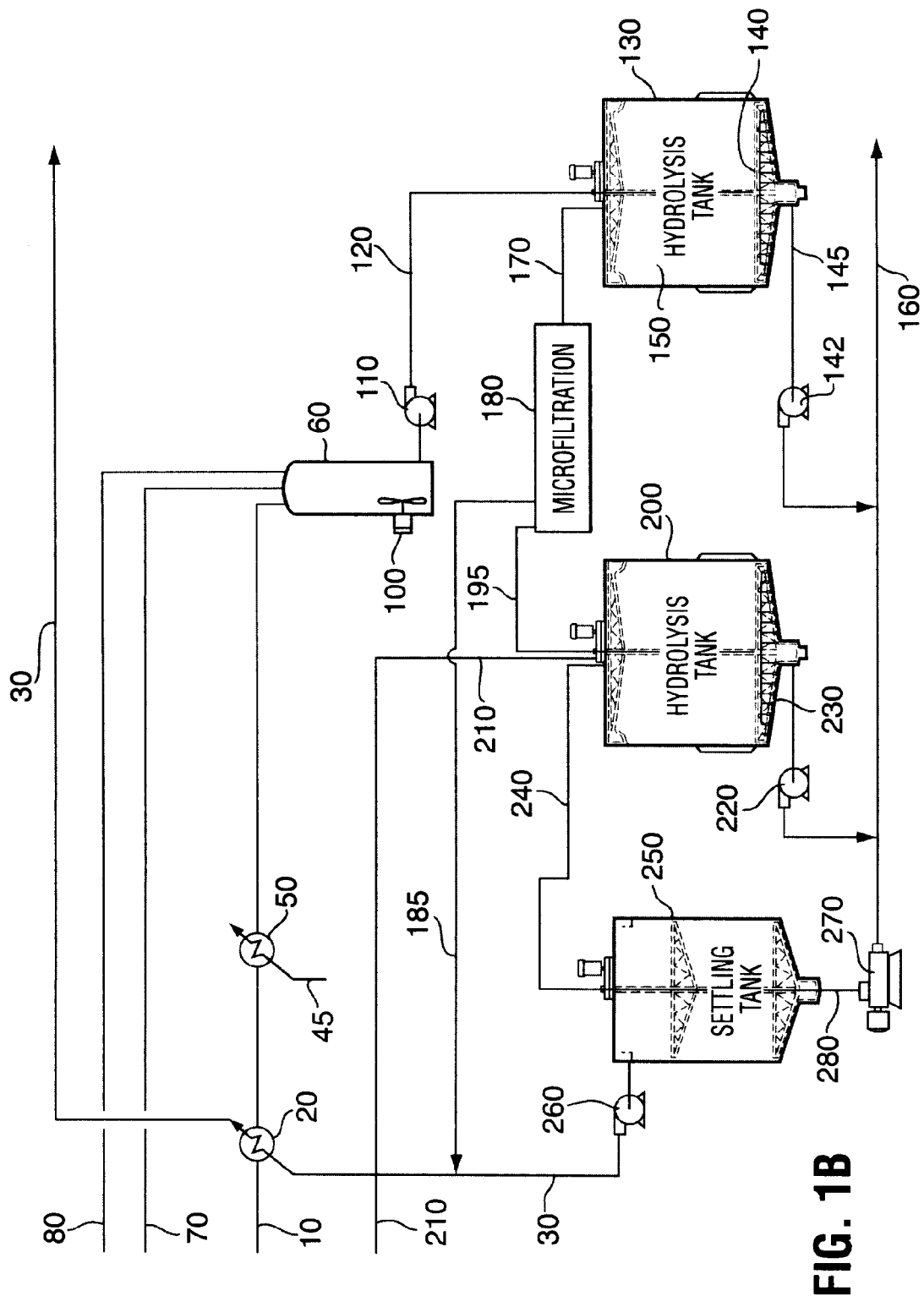
FIG. 1B shows a process flow diagram illustrating the steps of processing the lignocellulosic feedstock using upflow hydrolysis reactors.

A preferred method for carrying out the invention, which is not meant to be limiting, involves carrying out the hydrolysis in a settling reactor as described in WO 2006/063467 (the contents of which are herein incorporated by reference). An example of a hydrolysis system incorporating upflow hydrolysis reactors is shown in FIG. 1B. Reference numbers which are the same as in FIG. 1A indicate identical process steps. As shown in FIG. 1B, the aqueous slurry in line 120 is fed to hydrolysis reactor 130. This can be by a line that goes down through the middle of the reactor and then adds the slurry at the bottom, through distributor 140. Alternatively, the slurry feed can be directly to the distributor 140 at the bottom of the reactor. The aqueous slurry flows upward through the reactor with a vertical velocity that is low enough to allow fiber solids to settle. As a result, the aqueous phase traverses the reactor in a shorter time than the fiber solids. The bound cellulase and β-glucosidase remain in the reactor with the fiber solids, while the aqueous phase exits the reactor. The bound β-glucosidase ensures that cellobiose is converted to glucose within the hydrolysis, and does not inhibit cellulase enzymes. The unhydrolyzed solids are conveyed out of the reactor along with the aqueous phase at line 170 and are separated from the aqueous phase by microfiltration unit 180.

The separated solids obtained after a step of separating the fiber solids from the hydrolysis product comprising glucose may contain about 50% to about 80% moisture. The moisture content depends on the separation process used, the extent to which one chooses to de-water the solids and the efficiency of water removal. The separated solids may be washed with water to increase the amount of glucose removed.

After hydrolysis in a hydrolysis reactor with or without solids retention, the fiber solids are separated, re-suspended and the hydrolysis continued. The fiber solids are resuspended in an aqueous phase which is compatible for further hydrolysis of the re-suspended slurry. The aqueous solution used for re-suspension of the solids is preferably water, although other aqueous solutions may be used. The water may be fresh water, process water, or steam condensate. The amount of aqueous solution added for resuspension may be the same as was present in the aqueous slurry prior to hydrolysis, or preferably is somewhat less. The minimum amount is that required to pump or convey and mix the slurry as needed. The re-suspended slurry will be free of glucose and other soluble inhibitors, or their concentrations significantly reduced. In the absence of glucose, cellobiose and inhibitors, or by decreasing their concentration, the step of further hydrolysis can be carried out with increased efficiency.

Referring again to FIG. 1A, the re-suspension may be carried out by introducing the separated solids via line 195 to a second hydrolysis reactor 200 along with water 210 and then re-suspending them to produce a re-suspended slurry. The solids may be re-suspended in the liquid at a solids concentration of between about 3% and about 30% (w/w), or any concentration therebetween, for example, from about 10% to about 20% (w/w) suspended solids, or any concentration therebetween. The concentration of suspended solids in the re-suspended slurry is preferably the same or somewhat higher than the concentration of suspended solids in the pretreated feedstock slurry prior to solids separation.

After the fiber solids are re-suspended, the hydrolysis is allowed to continue further to convert the cellulose to a hydrolysis product comprising glucose. Hydrolysis of the re-suspended slurry may be allowed to proceed for about another 12-120 hours; for example hydrolysis of the re-suspended slurry may be allowed to proceed for about 12, 18, 24, 30, 36, 42, 48, 54, 60, 66, 72, 90, or 120 hours. The bottom of the second hydrolysis reactor 200 may be tapered to provide a path in which the heaviest solids may settle and be removed by pump 220 via line 230. (See FIG. 1B). These solids may then be sent for lignin processing 160.

Generally, the pH of the re-suspended slurry is within a range of about 3.0 to about 7.0, or any pH range therebetween; preferably the pH is within a range of about 4.5 to about 5.5. However, the pH of the solution can be higher or lower than about 4.5 to 5.5 if the cellulase enzymes used are alkalophilic or acidophilic, respectively.

The temperature of the re-suspended solution is adjusted so that it is within the optimum range for the activity of the cellulase enzymes. Generally, a temperature of about 45° C. to about 55° C., or any temperature therebetween, is suitable for most cellulase enzymes. For example, the temperature of the slurry may be adjusted to about 45, 46, 47, 48, 49, 50, 51, 52, 53, 54 or 55° C. However, the temperature of the solution may be higher for thermophilic cellulase enzymes.

Referring to FIG. 1A, the hydrolyzed slurry, which comprises glucose in the aqueous phase and unhydrolyzed solids and any unhydrolyzed cellulose-containing particles in the fiber solids, may be withdrawn from the top of the second hydrolysis reactor 200 via line 240 and then introduced to a settling tank 250. The fiber solids settle to the bottom of the settler tank 250. The aqueous phase 30 comprising glucose may be removed via a pump. The unhydrolyzed solids may be pumped out of the settler tank 250 via line 280.

The term "hydrolysis product" refers to products produced during the enzymatic hydrolysis, including, but not limited to glucose that is present in the aqueous phase. In addition to glucose, the aqueous phase of the hydrolysis product may also comprise cellobiose, glucose oligomers, or a combination thereof. Small amounts of unconverted cellulose, as well as non-cellulosic materials, or other materials that are inert to cellulase, may be carried over into the aqueous phase. These solids may be separated from the glucose stream to produce a preparation that is free of solid particles.

Although the system described above employs two hydrolysis reactors, the process may be performed in more than two hydrolysis reactors.

It should also be appreciated that, after the second hydrolysis, the resulting hydrolyzed slurry may be subjected to further hydrolysis. This may involve separation of the solids phase from the hydrolyzed slurry and re-suspension of the separated solids to produce a re-suspended slurry. These steps may be repeated 1 to 5 times, or any number of times therebetween, preferably 1 to 2 times.

Furthermore, the separated solids may be sent to one or more than one upstream or downstream hydrolysis reactor throughout the processing steps. For example, a first portion of the separated solids may be recycled to an upstream reactor and a second portion of the separated solids may be added to a downstream reactor.

A stream comprising glucose obtained after the step of partial hydrolysis may be combined with a stream comprising glucose obtained from the continued hydrolysis of the re-suspended slurry to produce a combined sugar stream. For example, with reference to FIG. 1A, the aqueous solution containing glucose may be removed via line 185 and added to glucose stream 30. Alternatively, fermentation or further processing is carried out separately on the aqueous phase produced during the partial hydrolysis and the re-suspended hydrolysis.

The glucose produced by the hydrolysis of cellulose from the pretreated lignocellulosic feedstock may be fermented to ethanol. Fermentation of glucose and other sugars to ethanol may be performed by conventional processes known to those skilled in the art and may be effected by a variety of microorganisms including yeast and bacteria or genetically modified microorganisms, for example, but not limited to those described in WO 95/13362, WO 97/42307, or as described in Alcohol Production From Lignocellulosic Biomass: The Logen Process (in: The Alcohol Textbook, Nottingham University Press, 2000) which are herein incorporated by reference.

The present invention will be further illustrated in the following examples. However, it is to be understood that these examples are for illustrative purposes only, and should not be used to limit the scope of the present invention in any manner.

EXAMPLES

Example 1

Hydrolysis of Pretreated Feedstock with Cellulase Enzymes and β-Glucosidase Containing a CBD in an Upflow Hydrolysis Reactor With reference to FIG. 1B, the pretreated feedstock slurry is prepared from 91 t/hr of wheat straw at 20% moisture. The straw is ground to 20 mesh with a hammer mill and cooked with steam at 230° C. and 3314 kg/hr sulfuric acid 93% (w/w) diluted in 422,000 kg/hr of water in accordance with the teaching of Foody, U.S. Pat. No. 4,461,648. When exiting the pretreatment reactor, the pretreated lignocellulosic feedstock slurry 10 is cooled using a heat exchanger 20 that exchanges against an aqueous glucose stream 30 or other suitable fluid. The pretreated feedstock slurry 10 is then further cooled to a temperature of between about 45° C. and about 55° C. using a second fluid, for example, cold water 45 at heat exchanger 50. The pretreated feedstock slurry 10 is then pumped into a hydrolysis make-up tank 60, along with an aqueous solution of enzymes 70, which include cellulase enzymes from the fungus *Trichoderma* at a dosage of 19 IU/gram cellulose and a β-glucosidase enzyme comprising a CBD, made as described in Example 5, at a dosage of 145 IU/g cellulose. This is the feed to the hydrolysis tower. However, it should be noted that the enzymes 70 may also be added elsewhere; for example, the enzymes 70 may be added within any line that feeds the hydrolysis reactor. Ammonia 80 is also added to the slurry 10 at a rate of 1463 kg/hr immediately prior to enzyme addition to adjust the pH to between about 4.5 and 5.0. The contents of the hydrolysis make-up tank 60 are mixed with an agitator 100 and the slurry 10 is then is pumped out of the make-up tank 60 by pump 110, along pipe 120, to one of seven similar hydrolysis reactors, of which hydrolysis reactor 130 is one such reactor operated in parallel trains.

The hydrolysis reactor 130 comprises distributors 140 for maintaining a uniform distribution of the enzyme-treated slurry. The hydrolysis reactor 130 is an unmixed upflow settling reactor as described in WO 2006/063467. The reactor is a tank of diameter 60 feet and height 60 feet. The slurry 10 is added to the bottom of the hydrolysis reactor 130 at a rate of 300 gpm and a fiber solids concentration of about 10% (w/w). The tank is tapered to provide a path in which the heaviest solids settle and are removed by pump 142 via line 145. These solids may be sent for lignin processing via line 160, or recovered separately or discharged. The aqueous phase and fiber solids flow up the tank with the fiber solids settling and ascending the tank at a slower rate than the liquid.

The slurry exits the tank after a residence time of the aqueous phase of about 72 hours and of the fiber solids, which maintain a concentration of 12% (w/w), of about 130 hours. The cellulose conversion is about 95%. The hydrolyzed slurry 150, which comprises an aqueous phase of 60 g/L glucose and fiber solids comprising primarily unhydrolyzed cellulose as well as lignin and silica, is removed from the top of the hydrolysis reactor 130 via line 170 and introduced to a microfiltration unit 180 at a rate of 300 gpm. The microfiltration unit 180 separates the fiber solids comprising cellulose, lignin and bound cellulase and β-glucosidase from the aqueous phase. The aqueous phase contains little enzyme with the glucose stream and is removed via line 185 and sent to fermentation to ethanol by yeast. The separated fiber solids containing bound cellulase and β-glucosidase 195 are suitable to be sent to a second hydrolysis reactor for further hydrolysis.

Example 2

Hydrolysis of Pretreated Feedstock with Cellulase Enzymes and β-Glucosidase Containing a CBD in an Upflow Hydrolysis Reactor with Continued Hydrolysis This example relates to the enzymatic hydrolysis of a pretreated feedstock with cellulase enzymes and β-glucosidase with a CBD, followed by separation of unhydrolyzed fiber solids from the aqueous phase and resuspension of the fiber solids. The re-suspended fiber solids, which contain the bound β-glucosidase enzyme and cellulase enzymes, are hydrolyzed in a second hydrolysis reactor.

Hydrolysis of pretreated feedstock with cellulase enzymes and β-glucosidase enzyme with a CBD is carried out in an upflow hydrolysis reactor as described in Example 1. However, in this case, the dimensions of the hydrolysis reactor are selected so that the liquid exits the tank after a residence time of about 24 hours with a cellulose conversion of about 55% to produce a partially-hydrolyzed slurry 150. The partially-hydrolyzed slurry 150, which comprises an aqueous phase of 30 g/L glucose and fiber solids comprising primarily unhydrolyzed cellulose, as well as lignin and silica, is removed from the top of the first hydrolysis reactor 130 via line 170 and introduced to a microfiltration unit 180 at a rate of 900 gpm.

The microfiltration unit 180 separates the solids comprising cellulose, lignin, bound cellulase and β-glucosidase from the aqueous phase of the partially-hydrolyzed slurry. The aqueous phase contains little enzyme with the glucose stream and is removed via line 185 and added to glucose stream 30. The separated solids 195 containing bound cellulase and β-glucosidase are introduced to a second hydrolysis reactor 200 along with water 210 to produce a re-suspended slurry and then fed to the second hydrolysis reactor 200 which is also an upflow hydrolysis reactor. The feed rate to the second reactor is about 450 gpm and the liquid residence time is about 48 hours. Similar to the first hydrolysis reactor 130, the bottom of the second hydrolysis reactor 200 is tapered to provide a path in which the heaviest solids settle and are removed by pump 220 via line 230. These solids may then be sent for lignin processing via line 160 or removed separately or discharged.

Glucose, and any unhydrolyzed cellulose-containing and lignin-containing particles are then withdrawn from the top of the second hydrolysis reactor 200 via line 240 and are introduced to a settling tank 250. The solids settle in the bottom of the settler tank 250 and the hydrolysis product stream 30 comprising glucose is removed via pump 260. The settled solids are pumped out of the settler tank 250 by pump 270 via line 280. These solids are then sent for lignin processing via line 160. Stream 30 is sent to the first heat exchanger or for fermentation to ethanol by yeast.

Example 3

Cellulose Hydrolysis by Enzyme Including
β-Glucosidase with Cellulose Binding Domain
(CBD)

This example illustrates the hydrolysis of pretreated cellulose with solids separation and resuspension of the substrate. The performance of the hydrolysis is better with β-glucosidase with a CBD present than without a CBD.

Pretreated wheat straw was prepared by continuous pretreatment with 0.6% sulfuric acid (w/w) on feedstock, heated to 185° C. with steam for 3 minutes. The pretreated feedstock was washed with an excess of water and vacuum filtered to remove most of the water. The washed feedstock cake contained 30% solids, and the solids contained 51% cellulose, with the balance being composed primarily xylan, lignin and silica.

Two cellulase enzyme mixtures from *Trichoderma* submerged culture fermentations were used in this experiment. Both mixtures contained enhanced levels of β-glucosidase to ensure cellobiose did not accumulate during the hydrolysis. The level of β-glucosidase was enhanced by the methods of White and Hindle, U.S. Pat. No. 6,015,703. One mixture contained 163 g/L protein and 131 IU/mL filter paper cellulase activity. This batch ("conventional") contained native β-glucosidase lacking a cellulose binding domain. The β-glucosidase activity was measured by the standard assay of Ghose (1987) as 1235

IU/mL. A second batch ("βg with CBD") contained 32.5 g/L protein, 20.7 IU/mL filter paper cellulase activity, and 250 IU/mL β-glucosidase activity. Example 5 describes the preparation of β-glucosidase with CBD in more detail.

Cellulose hydrolyses were carried out by using 250 mL screw top flasks. The total hydrolysis weight was 100 g per flask, with pretreated wheat straw at a concentration corresponding to 5% cellulose, enzyme added at a dosage of 16 or 24 mg protein per gram of cellulose, and the balance containing 50 mM sodium citrate buffer, pH 4.8, which contained 0.5% sodium benzoate as a preservative. Before adding the enzyme, the pretreated wheat straw substrate was hydrated overnight in the buffer at 50° C. with the flasks shaking. During the hydrolysis, the flasks were shaken at 250 rpm in a 50° C. gyratory shaker.

For hydrolyses with filtration and resuspension, the flasks were removed from the shaker at 24 hours and the contents vacuum-filtered over glass microfiber filter paper. The filtrate volume was measured as 40-50 mL and the filtrate was replaced by an equal volume of 50 mM sodium citrate buffer, pH 4.8. Similar to the hydrolysis carried out prior to filtration and resuspension, the shaken hydrolysis was then continued for 96 hours. For conventional hydrolyses, the hydrolysis runs were carried out shaken for 120 hours without filtration or resuspension.

For all hydrolyses, 800 μL samples were periodically taken and transferred into micro-centrifuge filters and centrifuged at 12,000 rpm for 2 minutes to separate the insoluble solids from the aqueous phase. The supernatant was recovered and used for glucose analysis. Most samples were checked to ensure cellobiose did not accumulate by boiling for 5 minutes prior to centrifugation.

Glucose concentrations in the supernatant were measured by an enzymatic method. Low (<1 g/L) cellobiose concentrations were confirmed by measurement on an HPLC. A cellulose assay based on hydrolysis with concentrated sulfuric acid was performed at the end of all hydrolysis runs and confirmed the concentration of unconverted cellulose based on glucose measurement.

Figure 2A:
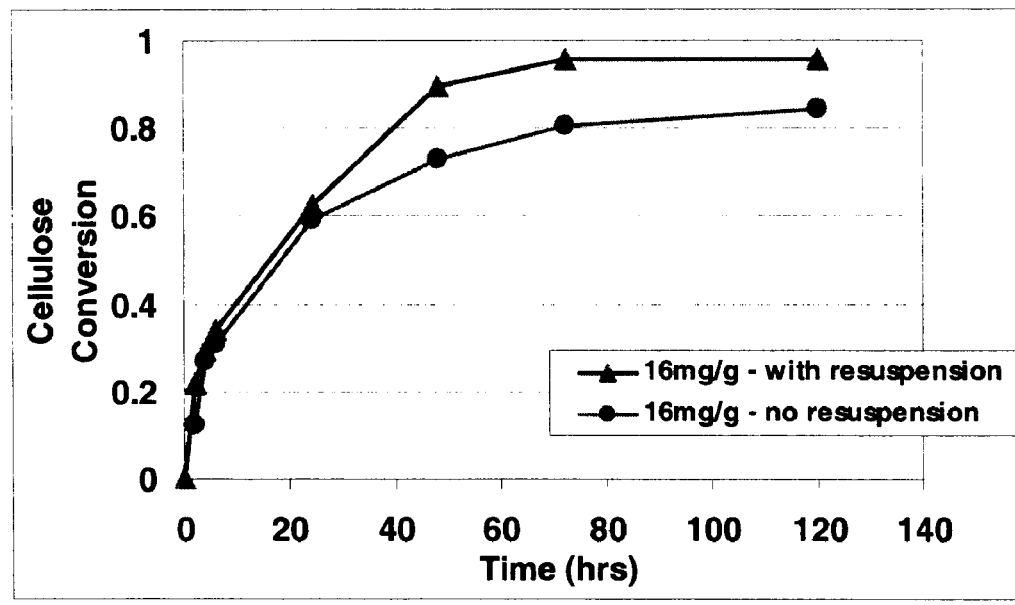
FIGS. 2A and 2B show the hydrolysis of 5% pretreated wheat straw cellulose by *Trichoderma* cellulase containing β-glucosidase with a CBD with and without resuspension. The hydrolysis with resuspension was filtered and re-suspended at 24 hours, while the hydrolysis without resuspension was run undisturbed.

FIG. 2A shows the results of hydrolysis by cellulase with β-glucosidase containing CBD, with cellulase dosages of 16 mg protein per gram cellulose. The re-suspended hydrolysis outperforms the conventional hydrolysis that was carried out without resuspension. The reason is that the filtration of the hydrolysis after 24 hours removes a significant amount of the glucose present. By removing the glucose, the end product inhibition of the cellulase is removed, and the hydrolysis proceeds at a higher rate and reaches a higher level of conversion than in the presence of glucose in the conventional hydrolysis. The β-glucosidase, which is necessary for an effective hydrolysis, is bound to the cellulose and is carried into the resuspension hydrolysis.

Figure 2B:
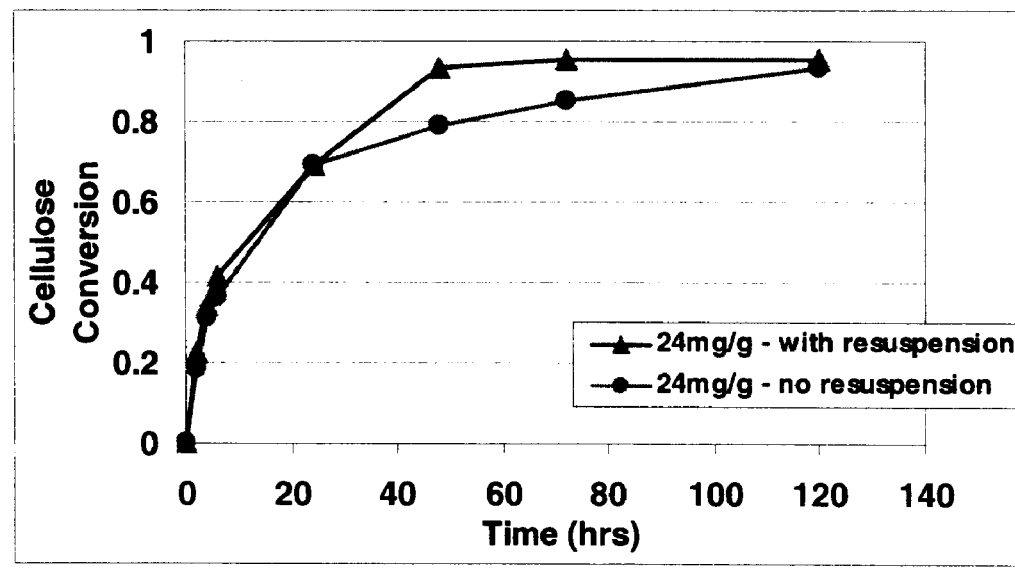

FIG. 2B shows a similar result as FIG. 2A, except the enzyme dosage is 24 mg/g instead of 16 mg/g in FIG. 2A.

Figure 3:
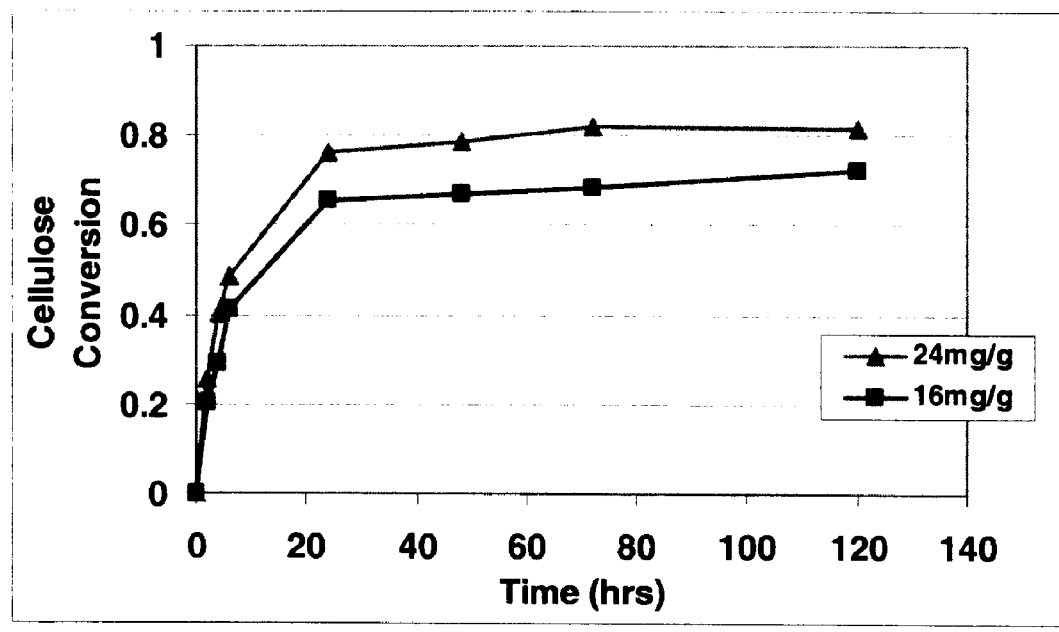
FIG. 3 shows the hydrolysis of 5% pretreated wheat straw cellulose by *Trichoderma* cellulase containing native β-glucosidase which lacks a CBD. The hydrolyses were filtered and re-suspended at 24 hours.

FIG. 3 shows hydrolysis with a conventional cellulase, where the β-glucosidase lacks a CBD. The hydrolyses were carried out for 24 hours at dosages of 16 and 24 mg/g. At this point, the slurries were filtered and the hydrolyses re-suspended and continued. The rate of hydrolysis after re-suspension is very low, with very little glucose produced. The reason for this low rate of hydrolysis is that the β-glucosidase lacks a CBD and does not bind to the cellulose, but rather is lost to the filtrate during filtration. The buildup of cellobiose inhibits the cellulase and slows down the rate of hydrolysis.

Example 4

Binding of β-Glucosidase with CBD to Bleached
Wheat Straw Cellulose

β-glucosidase and β-glucosidase containing a CBD were purified from whole cellulase mixtures by anion exchange chromatography followed by cation exchange chromatography. The purified proteins were incubated with 2.56 g/L pretreated wheat straw adjusted to pH 4.8 with citrate buffer or with pH 4.8 citrate buffer alone for 30 minutes at 4° C. or 50° C. Following incubation, the samples were centrifuged and the supernatant fractions were analyzed by SDS-PAGE (FIGS. 4A and 4B).

Figure 4A:
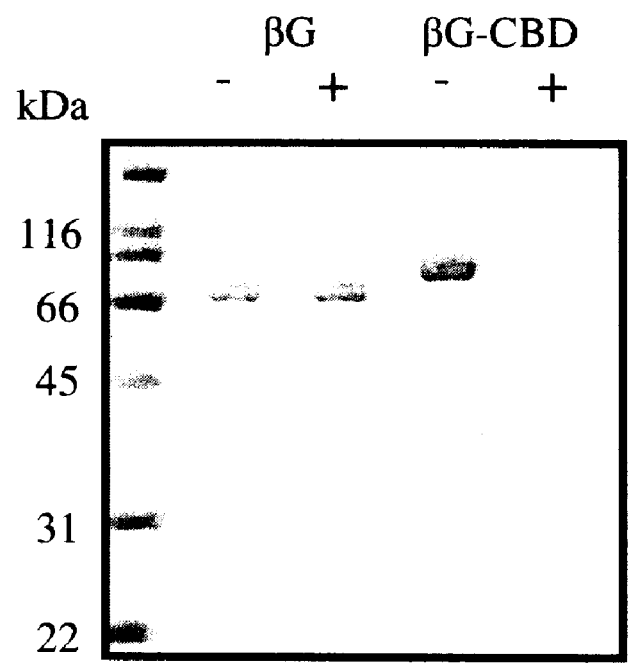
FIGS. 4A and 4B are SDS-PAGE gels of purified β-glucosidase without a CBD (βG) and β-glucosidase with a CBD (βG-CBD) after incubation in the presence (+) or absence (−) of pretreated wheat straw.
Figure 4B:
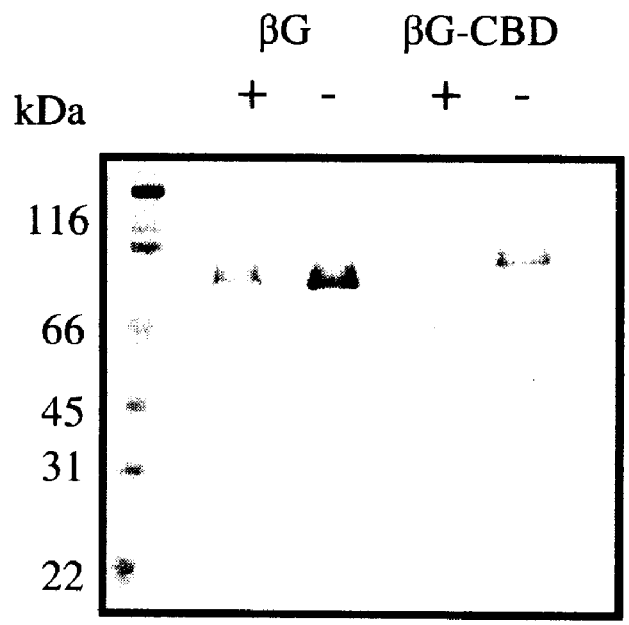

As shown in FIG. 4A, after incubation at 4° C. in the presence and absence of pretreated wheat straw, identical amounts of β-glucosidase were detected in the supernatant. This is indicated by the bands at 66 kDa and indicates that β-glucosidase lacking a CBD did not bind to the pretreated wheat straw. In contrast, purified β-glucosidase-CBD completely bound to pretreated wheat straw and was not detected in the supernatant, as indicated by the band at 70 kDa in the absence of pretreated wheat straw, and the absence of the band in the presence of pretreated wheat straw. This shows that the CBD is required for β-glucosidase to bind to the fiber solids. Similar results were observed at 50° C. (FIG. 4B).

Example 5

Expression of a β-Glucosidase/CBD Fusion in *Trichoderma reesei*

This example describes the isolation of genomic DNA from *Trichoderma reesei* strain M2C38 and genetically modified derivatives, the construction of genomic DNA libraries, the cloning of various genes, genetic constructs from *Trichoderma reesei* strain M2C38, and the transformation and expression of β-glucosidase/CBD genetic constructs in *Trichoderma reesei* strain BTR213.

*Trichoderma reesei* strains M2C38 and BTR213 are proprietary strains of Iogen Corporation which were derived from *Trichoderma reesei* RutC30 (ATCC 56765, Montenecourt and Eveleigh, *Adv. Chem. Ser.*, 1979, 181: 289-301), which was, in turn, derived from *Trichoderma reesei* Qm6A (ATCC 13631 Mandels and Reese, *J. Bacteriol.*, 1957, 73: 269-278).

In this example, restriction endonucleases, T4 DNA polymerase, T4 DNA ligase and Klenow fragment of *E. coli* DNA polymerase 1 were purchased from Gibco/BRL, New England Biolabs, Boehringer Mannheim or Pharmacia and used as recommended by the manufacturer. Pwo polymerase with proof-reading activity (Boehringer Mannheim) was used in all polymerase-chain reactions (PCR) according to the manufacturer's protocol. Hygromycin B was purchased from CalBiochem.

5.1 Cloning of the *T. reesei* bgl1, cbh1, cbh2, xln2 and pgk genes.

To isolate genomic DNA, 50 mL of Potato Dextrose Broth (Difco) was inoculated with *T. reesei* spores collected from a Potato Dextrose Agar plate with a sterile inoculation loop. The cultures were shaken at 200 rpm for 2-3 days at 28° C. The mycelia were filtered onto a GFA glass microfibre filter (Whatman) and washed with cold deionized water. The fungal cakes were frozen in liquid nitrogen crushed into a powder with a pre-chilled mortar and pestle; 0.5 g of powdered biomass were re-suspended in 5 mL of 100 mM Tris, 50 mM EDTA, pH 7.5 plus 1% sodium dodecyl sulphate (SDS). The lysate was centrifuged (5000 g for 20 min, 4° C.) to pellet cell debris. The supernatant was extracted with 1 volume buffer-(10 mM Tris, 1 mM EDTA, pH 8.0)-saturated phenol, followed by extraction with 1 volume of buffer-saturated phenol:chloroform:isoamyl alcohol (25:24:1) in order to remove soluble proteins. DNA was precipitated from the solution by adding 0.1 volumes of 3 M sodium acetate, pH 5.2 and 2.5 volumes of cold 95% ethanol. After incubating for at least 1 hour at −20° C., the DNA was pelleted by centrifugation (5000 g for 20 min, 4° C.), rinsed with 10 mL 70% ethanol, air-dried and re-suspended in 1 mL 10 mM Tris, 1 mM EDTA, pH 8.0. RNA was digested by the addition of Ribonuclease A (Boehringer Mannheim) added to a final concentration of 0.1 mg/mL and incubated at 37° C. for 1 hour. Sequential extractions with 1 volume of buffer-saturated phenol and 1 volume of buffer-saturated phenol:chloroform:isoamyl alcohol (25:24:1) were used to remove the ribonuclease from the DNA solution. The DNA was again precipitated with 0.1 volumes of 3 M sodium acetate, pH 5.2 and 2.5 volumes of cold 95% ethanol, pelleted by centrifugation, rinsed with 70% ethanol, air-dried and re-suspended in 50 µl of 10 mM Tris, 1 mM EDTA, pH 8.0. The concentration of DNA was determined by measuring the absorbance of the solution at 260 nm (p. C1 in Sambrook, Fritsch and Maniatis, "Molecular Cloning: A Laboratory Manual, Second Edition", Cold Spring Harbor Press 1989, hereafter referred to as Sambrook et al.).

Two plasmid libraries and one phage library were constructed using genomic DNA isolated from *T. reesei* strain M2C38. The plasmid libraries were constructed in the vector pUC119 (Viera and Messing, "Isolation of single-stranded plasmid DNA", Methods Enzymol. 153:3, 1987) as follows: 10 µg genomic DNA was digested for 20 hrs at 37° C. in a 100 µL volume with 2 units/µg of HindIII, BamH1 or EcoR1 restriction enzymes. The digested DNA was fractionated on a 0.75% agarose gel run in 0.04M Tris-acetate, 1 mM EDTA and stained with ethidium bromide. Gel slices corresponding to the sizes of the genes of interest (based on published information and Southern blots) were excised and subjected to electro-elution to recover the DNA fragments (Sambrook et al., pp. 6.28-6.29). These enriched fractions of DNA were ligated into pUC119 in order to create gene libraries in ligation reactions containing 20-50 µg/mL DNA in a 2:1 molar ratio of vector:insert DNA, 1 mM ATP and 5 units T4 DNA ligase in a total volume of 10-15 µl at 4° C. for 16 h. *Escherichia coli* strain HB101 was electroporated with the ligation reactions using the Cell Porator System (Gibco/BRL) following the manufacturer's protocol and transformants selected on LB agar containing 70 µg/mL ampicillin.

*E. coli* HB101 transformants harboring cbh1, cbh2 or bgl1 clones from the recombinant pUC119-Hind III, -BamH1 or -EcoR1 libraries were identified by colony lift hybridization: 1-3×10$^4$ colonies were transferred onto HyBond™ nylon membranes (Amersham); membranes were placed colony-side up onto blotting paper (VWR 238) saturated with 0.5 M NaOH, 1 M NaCl for 5 minutes to lyse the bacterial cells and denature the DNA; the membranes were then neutralized by placing them colony-side up onto blotting paper (VWR 238) saturated with 1.5 M Tris, pH 7.5 plus 1 M NaCl for 5 min; the membranes were allowed to air-dry for 30 min and the DNA was then fixed to the membranes by baking at 80° C. for 2 h.

$^{32}$P-labelled probes were prepared by PCR amplification of short (0.7-1.5 kB) fragments of the bgl1, cbh1 and cbh2 coding regions from the enriched pool of HindIII, BamH1 or EcoR1 fragments, respectively, in a labelling reaction containing 10-50 ng target DNA, 0.2 mM each d(GCT)TP, 0.5 µM dATP, 20-40 µCi α-$^{32}$P-dATP, 10 pmole oligonucleotide primers and 0.5 units Taq polymerase in a total volume of 20 µL. The reaction was subjected to 6-7 cycles of amplification (95° C., 2 min; 56° C., 1.5 min; 70° C., 5 min). The amplified, $^{32}$P-labelled DNA was precipitated by the addition of 0.5 mL 10% (w/v) trichloroacetic acid and 0.5 mg yeast tRNA. The DNA was pelleted by microcentrifugation, washed twice with 1 mL 70% ethanol, air-dried and re-suspended in 1M Tris pH7.5, 1 mM EDTA.

Nylon membranes onto which the recombinant pUC119 plasmids had been fixed were prehybridized in heat-sealed bags for 1 h at 60-65° C. in 1 M NaCl, 1% SDS, 50 mM Tris, 1 mM EDTA pH 7.5 with 100 μg/mL denatured sheared salmon sperm DNA. Hybridizations were performed in heat-sealed bags in the same buffer with only 50 μg/mL denatured sheared salmon sperm DNA and $5 \times 10^6$-$5 \times 10^7$ cpm of denatured bgl1, cbh1 or cbh2 probe for 16-20 h at 60-65° C. Membranes were washed once for 15 minutes with 1 M NaCl, 0.5% SDS at 60° C., twice for 15 minutes each with 0.3M NaCl, 0.5% SDS at 60° C. and once for 15 minutes with 0.03M NaCl, 0.5% SDS at 55° C. Membranes were again placed in heat-sealed bags and exposed to Kodak RP X-ray film to 16-48 h at −70° C. The X-ray film was developed following the manufacturer's protocols. Colonies giving strong or weak signals were picked and cultured in 2×YT media supplemented with 70 μg/mL ampicillin. Plasmid DNA was isolated from these cultures using the alkaline lysis method (Sambrook, et al., pp. 1.25-1.28) and analyzed by restriction digest, Southern hybridization (Sambrook, et al., pp. 9.38-9.44) and PCR analysis (Sambrook, et al., pp. 14.18-14.19).

Clones carrying the bgl1 gene were identified by colony lift hybridization of the pUC119-Hind III library with a 1.0 kb bgl1 probe prepared using oligonucleotide primers designed to amplify bp 462-1403 of the published bgl1 sequence (Barnett, Berka, and Fowler, in "Cloning and Amplification of the Gene Encoding an Extracellular β-glucosidase from *Trichoderma reesei*: Evidence for Improved Rates of Saccharification of Cellulosic Substrates" Bio/Technology, Volume 9, June 1991, p. 562-567, herein referred to as "Barnett, et al."). A bgl1 clone, pJEN200, was isolated containing 6.0 kb Hind III fragment corresponding to the promoter, structural gene and termination sequences. Clones carrying the cbh1 gene were identified by colony lift hybridization of the pUC119-BamH1 library with a 0.7 kb cbh1 probe prepared using oligonucleotide primers designed to amplify bp 597-1361 of the published cbh1 sequence (Shoemaker, Schweikart, Ladner, Gelfand, Kwok, Myambo and Innis, "Molecular cloning of exo-cellobiohydrolase 1 derived from *Trichoderma reesei* strain L27", Bio/Technology 1: 691-696, 1983 hereafter referred to as Shoemaker et al.). A cbh1 clone, pCOR132 was isolated containing a 5.7 kb BamH1 fragment corresponding to the promoter (4.7 kb) and 1 kb of the cbh1 structural gene. From this, a 2.5 kb EcoR1 fragment containing the cbh1 promoter (2.1 kb) and 5' end of the cbh1 coding region (0.4 kb) was subcloned into pUC119 to generate pCB152. Clones carrying the cbh2 gene were identified by colony lift hybridization of the pUC119-EcoR1 library with a 1.5 kb cbh2 probe prepared using oligonucleotide primers designed to amplify bp 580-2114 of the published cbh2 sequence (Chen, Gritzali and Stafford, "Nucleotide sequence and deduced primary structure of cellobiohydrolase II from *Trichoderma reesei*", Bio/Technology 5: 274-278, 1987, hereafter referred to as Chen et al.). A cbh2 clone, pZUK600 was isolated containing a 4.8 kb EcoR1 fragment corresponding to the promoter (600 bp), structural gene (2.3 kb) and terminator (1.9 kbp).

A phage library was constructed in the lambda vector λDASH (Stratagene, Inc.) as follows: genomic DNA (3 μg) was digested with 2, 1, 0.5 and 0.5 units/μg Bam HI for 1 hour at 37° C. to generate fragments 9-23 kB in size. The DNA from each digest was purified by extraction with 1 volume Tris-saturated phenol:choroform:isoamyl alcohol (25:24:1) followed by precipitation with 10 μl 3M sodium acetate, pH 5.2 and 250 μl 95% ethanol (−20° C.). The digested DNA was pelleted by microcentrifugation, rinsed with 0.5 mL cold 70% ethanol, air-dried and re-suspended in 10 μL sterile, deionized water. Enrichment of DNA fragments 9-23 kB in size was confirmed by agarose gel electrophoresis (0.8% agarose in 0.04 M Tris-acetate, 1 mM EDTA). Digested DNA (0.4 μg) was ligated to 1 μg λDASH arms predigested with BamH1 (Stratagene) in a reaction containing 2 units T4 DNA ligase and 1 mM ATP in a total volume of 5 μL at 4° C. overnight. The ligation mix was packaged into phage particles using the GigaPack® II Gold packaging extracts (Stratagene) following the manufacturer's protocol. The library was titred using the *E. coli* host strain XL1-Blue MRA (P2) and found to contain $3 \times 10^5$ independent clones.

Digoxigen-11-dUTP labelled probes were prepared from PCR amplified coding regions of the cbh1, xln2 and pgk genes by random prime labelling using the DIG Labelling and Detection kit (Boehringer Mannheim) and following the manufacturer's protocols. Genomic clones containing the cbh1, xln2 and pgk genes were identified by plaque-lift hybridization of the λDASH library. For each gene of interest, $1 \times 10^4$ clones were transferred to Nytran® (Schleicher and Schull) nylon membranes. The phage particles were lysed and the phage DNA denatured by placing the membranes plaque-side up on blotting paper (VWR238) saturated with 0.5 M NaOH, 1 M NaCl for 5 minutes; the membranes were then neutralized by placing them plaque-side up onto blotting paper (VWR238) saturated with 1.5 M Tris, pH 7.5 plus 1 M NaCl for 5 min; the membranes were allowed to air-dry for 30 min and the DNA was then fixed to the membranes by baking at 80° C. for 2 hours. The membranes were prehybridized in heat-sealed bags in a solution of 6×SSPE, 5×Denhardt's, 1% SDS plus 100 mg/mL denatured, sheared salmon sperm DNA at 65° C. for 2 h. The membranes were then hybridized in heat-sealed bags in the same solution containing 50 μg/mL denatured, sheared salmon sperm DNA and 0.5 μg of digoxigen-dUTP labelled probes at 65° C. overnight. The membranes were washed twice for 15 min in 2×SSPE, 0.1% SDS at RT, twice for 15 minutes in 0.2×SSPE, 0.1% SDS at 65° C. and once for 5 minutes in 2×SSPE. Positively hybridizing clones were identified by reaction with an anti-digoxigenin/alkaline phosphatase antibody conjugate, 5-bromo-4-chloro-3-indoyl phosphate and 4-nitro blue tetrazolium chloride (Boehringer Mannheim) following the manufacturer's protocol. Positively hybridizing clones were purified further by a second round of screening with the digoxigen-dUTP labelled probes. Individual clones were isolated and the phage DNA purified as described in Sambrook et al. (1989) pp. 2.118-2.121, with the exception that the CsCl gradient step was replaced by extraction with 1 volume of phenol:choroform:isoamyl alcohol (25:24:1) and 1 volume of chloroform:isoamyl alcohol (24:1). The DNA was precipitated with 0.1 volumes of 3M sodium acetate, pH 5.2 and 2.5 volumes cold 95% ethanol. The precipitated phage DNA was washed with 0.5 mL cold 70% ethanol, air-dried and re-suspended in 50 μL 10 mM Tris, 1 mM EDTA pH8.0. Restriction fragments containing the genes of interest were identified by restriction digests of the purified phage DNA and Southern blot hybridization (Sambrook, et al., pp. 9.38-9.44) using the same digoxigen-dUTP labelled probes used to screen the λDASH library. The membranes were hybridized and positively hybridizing fragments visualized by the same methods used for the plaque lifts. Once the desired restriction fragments from each λDASH clone were identified, the restriction digests were repeated, the fragments were resolved on a 0.8% agarose gel in TAE and the desired bands excised. The DNA was eluted from the gel slices using the Sephaglas B and Prep Kit (Pharmacia) following the manufacturer's protocol.

Clones carrying the cbh1 gene were identified by colony lift hybridization of the λDASH library (example 2) with a cbh1 probe comprising bp 45-2220 of the published cbh1 sequence (Shoemaker et al.). A 1.8 kb BamH1 fragment containing the 3' end of the cbh1 coding region (0.5 kb) and the cbh1 terminator (1.3 kb) was isolated by restriction digestion of phage DNA purified from a λDASH cbh1 clone. This fragment was subcloned into the BamH1 site of the *E. coli* plasmid vector pUC119 to generate the plasmid pCB1Ta. Clones carrying the xln2 gene were identified by colony lift hybridization of the λDASH library (example 2) with a xln2 probe comprising bp 100-783 of the published xln2 sequence (Saarelainen, Paloheimo, Fagerstrom, Suominen and Nevalainen, "Cloning, sequencing and enhanced expression of the *Trichoderma reesei* endoxylanase II (pI 9) gene xln2", Mol. Gen. Genet. 241: 497-503, 1993, hereafter referred to as Saarelainen et al.). A 5.7 kb Kpn1 fragment containing the promoter (2.3 kb), coding region (0.8 kb) and terminator (2.6 kb) the xln2 gene was isolated by restriction digestion of phage DNA purified from a λDASH xln2 clone. This fragment was subcloned into the Kpn1 site of pUC119 to generate the plasmid pXYN2K-2. Clones carrying the pgk gene were identified by colony lift hybridization of the λDASH library (example 2) with a pgk1 probe comprising bp 4-1586 the published pgk sequence (Vanhanen, Penttila, Lehtovaara and Knowles, "Isolation and characterization of the 3-phosphoglycerate kinase gene (pgk) from the filamentous fungus *Trichoderma reesei*", Curr. Genet. 15: 181-186, 1989). A 5.0 kb EcoR1 fragment containing the promoter (2.9 kb), coding region (1.6 kb) and terminator (0.5 kb) the pgk gene was isolated by restriction digestion of phage DNA purified from a λDASH pgk clone. This fragment was subcloned into the EcoR1 site of pUC119 to generate the plasmid pGK5.0.

5.2 Construction of β-Glucosidase Overexpression Vector PC/XBG-CBD-TV

This Example describes the construction of a vector designed to express a fusion protein of the mature β-glucosidase coding region and a peptide comprising the linker-cellulose binding domain of *Trichoderma* cellobiohydrolase I. In this construct, the expression of the fusion protein is directed by the *Trichoderma* cellobiohydrolase I (cbh1) promoter and xylanase 2 (xln2) secretion signal peptide.

The β-glucosidase coding region less the C-terminal alanine residue (bp 474-2679) was amplified with Pwo polymerase from the genomic bgl1 clone pJEN200 using primers to insert an Xba1 site directly upstream of bp 474 in the published bgl1 sequence (Barnett et al.) and a Kpn1 site at bp 2676, which is one codon away from the stop codon. This amplified fragment was subcloned without digestion into the Sma1 site of pUC19 to generate the plasmid pBgns1. The bgl1 fragment lacking the stop codon was released from pBgns1 by digestion with Xba1 and Kpn1 and inserted into pCB219N digested with Xba1 and Kpn1 to generate pBgns2. To make pCB219N, a cbh2 terminator fragment was amplified from the pZUK600 template using a primer homologous to bp 2226-2242 of the published 3' untranslated region of the cbh2 gene (Chen et al., 1987) containing a Kpn1 site at the 5' end and the pUC forward primer (Cat. No. 1224, New England Biolabs) which anneals downstream of the EcoR1 site at the 3' end of cbh2 in pZUK600. This fragment was digested at the engineered Kpn1 and EcoR1 sites and inserted into the corresponding sites of pUC119 to generate pCB219. An EcoR1-Not1 adaptor (Cat. No. 35310-010, Gibco/BRL) was inserted into the unique EcoR1 site of pCB219 to generate pCB219N.

A 2.3 kb fragment containing the promoter and secretion signal of the xln2 gene (bp −2150 to +99 where +1 indicates the ATG start codon) was amplified with Pwo polymerase from the genomic xln2 subclone pXYN2K-2 using a xln2-specific primer containing a Nhe1 site directly downstream of bp102 of the published xln2 sequence (Saarelainen et al.) and the pUC reverse primer (Cat. No. 18432-013, Gibco/BRL) which anneals upstream of the Kpn1 site at the 5' end of the xln2 gene. This xln2 PCR product was digested with EcoR1 (which was amplified as part of the pUC119 polylinker from pXYN2K-2) and Nhe1 and inserted into the plasmid pBR322L, which was prepared from the plasmid pBR322 by insertion of an Sph1-Not1-Sal1 linker between the Sph1 and Sal1 sites. The EcoR1 at the 5' end of the xln2 promoter in the resulting plasmid, pBR322LXN, was then blunted with Klenow and Spe1 linkers (Cat. No. 1086, New England Biolabs) were added to generate pBR322SpXN. A 1.2 kb HindIII fragment comprising bp −1399 to −204 of the cbh1 promoter was isolated by HindIII digestion of the cbh1 genomic subclone pCB152. This fragment was used to replace the HindIII fragment comprising bp −1400 to bp −121 of the xln2 promoter in the vector pBR322SpXN to generate the plasmid pBR322C/X.

The pBgns2 plasmid was cut with XbaI and NotI and a 4.2 kb fragment, containing the bgl1 coding region lacking the stop codon followed by the cbh2 terminator, was isolated. This fragment was inserted into the plasmid pBR322C/X cut with NheI and NotI (NheI and XbaI have compatible overhangs). This cloning resulted in an expression cassette from which the mature β-glucosidase lacking the stop codon can be expressed under the control of the cbh1 promoter and the xln2 secretion signal peptide. This expression cassette plasmid is pC/XBgns and has a unique Kpn1 site between the bgl1 coding region and the cbh2 terminator.

To obtain the cbh1 linker and CBD region, a DNA fragment comprising bp1665 to bp 1882 of the published cbh1 gene (Shoemaker, et al.) was amplified by PCR using primers to insert Kpn1 and Spe1 sites at both the 5' end and a Kpn1 site at the 3' end of the fragment. The 5' Kpn1 site is located in order to make a precise fusion between the reading frame between the bgl1 coding region in pC/XBgns and the reading frame of the cbh1 linker+CBD. The 3' Kpn1 site is located just after the stop codon of the native cbh1 coding region. This 215 by PCR product was digested with Kpn1 and inserted into the unique Kpn1 site of pC/XBgns, to produce the final expression cassette plasmid, pC/XBg-CBD. As a result of the insertion of the restriction sites, the final fusion protein expressed by this construct will contain three extra amino acids (Pro-Thr-Ser) between Val713 of the bgl1 coding sequence and the Ile474 of the cbh1 coding region.

The *E. coli* hygromycin phosphotransferase gene (hph) used as a selectable marker for *T. reesei* was amplified with Pwo polymerase from the plasmid pVU1005 (Van den Elzen, Townsend, Lee and Bedbrook, "A chimaeric hygromycin resistance gene as a selectable marker in plant cells", Plant Mol. Biol. 5: 299-302, 1989). The primers were designed to introduce Sph1 and Kpn1 sites at the 5' and 3' ends of the hph coding region (bp 211-1236 of the published hph sequence, Gritz and Davies, "Plasmid-encoded hygromycin b resistance: the sequence of hygromycin B phosphotransferase gene and its expression in *Escherichia coli* and *Saccharomyces cerevisiae*" Gene 25: 179-188, 1983), respectively. The PCR product was digested with Sph1 and Kpn1 and inserted into the corresponding sites in the polylinker region of pUC119. The resulting plasmid, pHPT100 was used as the starting plasmid for the construction of the selection cassette. Two new linker regions were introduced into this plasmid to facilitate the insertion of the promoter and terminator fragments required to express the hph gene in a *Trichoderma* host. A HindIII-XbaI-XhoI-SphI linker was inserted between the HindIII and SphI sites at the 5' end of the hph sequence and a KpnI-NotI-SacI linker which was inserted between the KpnI and SacI sites at the 3' end of the hph sequence. This construct was designated as pHPT102. The primers used to amplify the pgk promoter (Vanhanen, Saloheimo, Ilmen, Knowles and Penttila, "Promoter structure and expression of the 3-phosphoglycerate kinase gene (pgk1) of *Trichoderma reesei*", Gene 106: 129-133, 1991) were designed to introduce an XhoI site and a SphI site at positions −970 and +1 of the promoter respectively. These sites were subsequently used to insert the pgk promoter into the XhoI and SphI sites of pHPT102 to generate pHPT115. A 1.3 kb cbh1 terminator fragment was amplified with Pwo polymerase from pCB1Ta using a primer annealing to the 3' untranslated region of cbh1 (bp 1864-1899 of the published cbh1 sequence) containing a Kpn1 site at bp1877-1882 and the pUC reverse primer (Cat. No., 18432-013, Gibco/BRL) which anneals downstream of the EcoR1 site at the 3' end of the cbh1 terminator in pCB1Ta. The cbh1 terminator PCR product was digested with Kpn1 and inserted into the unique Kpn1 site of pHPT115 to generate the selection cassette plasmid pHPT136.

To make the transformation vector, the 5.8 kb expression cassette comprising a distal 5' region of the xln2 promoter, bp −1399 to −204 of the cbh1 promoter, bp −121 to +99 of the xln2 promoter and secretion signal peptide, the coding region for the β-glucosidase/CBD fusion and the cbh2 terminator was isolates from pC/XBg-CBD by digestion with Not1, blunting of the Not1 site with Klenow DNA polymerase, and digestion with Spe1. This 5.8 kb Spe1/Not1 fragment was inserted between the unique upstream of the hph selection cassette of pHPT136 which had been digested with Xho1, blunted with Klenow DNA polymerase and digested with Xba1 (Spe1 and Xba1 have compatible overhangs). The final transformation vector, pC/XBg-CBD-TV, was linearized at the unique Not1 site at the 3' end of the cbh1 terminator in the hph selection cassette and introduced as a linear vector into *T. reesei* BTR213 via microprojectile bombardment as described below.

5.3 Transformation of *T. reesei* BTR213 Via Microprojectile Bombardment

The Biolistic PDS-1000/He system (BioRad; E.I. DuPont de Nemours and Company) was used to transform spores of *T. reesei* strain BTR213 and all procedures were performed as recommended by the manufacturer. M-10 tungsten particles (median diameter of 0.7 um) were used as microcarriers. The following parameters were used in the optimization of the transformation: a rupture pressure of 1100 psi, a helium pressure of 29 mm Hg, a gap distance of 0.95 cm, a macrocarrier travel distance of 16 mm, and a target distance of 9 cm. Plates were prepared with $1 \times 10^6$ spores on Potato Dextrose Agar media (PDA). Bombarded plates were incubated at 28° C. Four hours post-bombardment, spores are subjected to primary selection by the overlaying of selective PDA media supplemented with 40 units/mL of HygB. The bombardment plates are incubated at 28° C. Transformants can be observed after 3-6 days growth; however, further incubation is necessary to achieve sporulation.

After sporulation has occurred, a secondary selection process is performed to isolate individual transformants. Spores are collected from the plate with an inoculating loop and re-suspended in sterile water. This suspension is then filtered through a sterile syringe plugged with glass microfibers. This allows the passage of spores while retaining unwanted mycelia. A determination of the concentration of spores in this suspension is required and subsequent dilutions are plated onto PDA plates supplemented with 0.75% Oxgall (Difco) and HygB (20 units/mL) to obtain 20-50 spores per plate. The Oxgall acts as a colony restrictor, thereby allowing the isolation of individual colonies on these secondary selection plates. Isolated colonies can be observed after 2-3 days.

5.4 Production off β-Glucosidase in Liquid Cultures

Individual colonies of *Trichoderma* are transferred to PDA plates for the propagation of each culture. Sporulation is necessary for the uniform inoculation of shake flasks which are used in testing the ability of the culture to produce the β-glucosidase and cellulase. The culture media is composed of the following:

TABLE 2

Components of the culture media

| Component | Concentration |
|---|---|
| $(NH_4)_2SO_4$ | 6.35 g/L |
| $KH_2PO_4$ | 4.00 g/L |
| $MgSO_4 \cdot 7H_2O$ | 2.02 g/L |
| $CaCl_2 \cdot 2H_2O$ | 0.53 g/L |
| Corn Steep Liquor | 6.25 g/L |
| $CaCO_3$ | 10.00 g/L |
| Carbon sources** | 5-10 g/L |
| Trace elements* | 1 mL/L |

*Trace elements solution contains 5 g/L $FeSO_4 \cdot 7H_2O$; 1.6 g/L $MnSO_4 \cdot H_2O$; 1.4 g/L $ZnSO_4 \cdot 7H_2O$.
**5 g/L glucose plus 10 g/L Solka floc (when the cbh1 or other cellulase promoter is used), 10 g/L xylan (when the xln2 promoter is used) or other carbon source compatible with the promoter directing the expression of the β-glucosidase. The carbon source can be sterilized separately as an aqueous solution at pH 2 to 7 and added to the remaining media.

The liquid volume per 1-liter flask is 150 mL, the initial pH is 5.5 and each flask is sterilized by steam autoclave for 30 minutes at 121° C. prior to inoculation.

For both native and transformed cells, spores are isolated from the PDA plates as described in Section 5.3 above and $1\text{-}2 \times 10^6$ spores are used to inoculate each flask. The flasks are shaken at 200 rpm at a temperature of 28° C. for a period of 6 days. The filtrate containing the secreted protein was collected by filtration through GF/A glass microfibre filters (Whatman). The protein concentration is determined using the Bio-Rad Protein Assay (Cat. No. 500-0001) using *Trichoderma* cellulase as a standard. β-glucosidase activity is determined as described in Ghose, 1987.

5.5 Production of β-glucosidase by *T. reesei* Strains BTR213 and 1059A Using Solka Floc Carbon Source The native strain BTR213 and the transformed strain from this host 1059A were cultured using the procedures of Example 5D with 10 g/L Solka floc and 5 g/L glucose as carbon sources. The results are shown in Table 2.

The native strain produced 0.19 IU of β-glucosidase per mg protein.

The transformant 1059A expressing the β-glucosidase/CBD fusion from the cbh1 promoter and xln2 secretion signal produced 7.6 IU/mg of β-glucosidase. This represents a 40-fold increase over the native strain, which represents the vast majority of the β-glucosidase.

TABLE 3

Production of β-glucosidase activity from *T. reesei* strains BTR213 and 1059A in 150 mL flask cultures

| Strain | Promoter | Secretion signal | β-glucosidase | β-glucosidase (IU/mg) |
|---|---|---|---|---|
| RutC30 | bgl1 | bgl1 | Native | 0.14 |
| RC-302 | cbh1 | xln2 | β-G/CBD fusion | 19 |

What is claimed is:

1. A process for the enzymatic hydrolysis of cellulose to produce a hydrolysis product comprising glucose from a pretreated lignocellulosic feedstock, the process comprising:
   (i) partially hydrolyzing an aqueous slurry of the pretreated lignocellulosic feedstock with an enzyme composition to produce a hydrolyzed slurry comprising glucose, glucose oligomers or a combination thereof, and unhydrolyzed fiber solids comprising cellulose and lignin, said enzyme composition comprising cellulase enzymes and at least one β-glucosidase enzyme comprising a cellulase binding domain that binds said β-glucosidase enzyme to said pretreated lignocellulosic feedstock;
   (ii) separating the unhydrolyzed fiber solids from the aqueous phase to produce separated fiber solids, wherein the cellulase enzymes and the at least one β-glucosidase enzyme comprising a cellulose binding domain bind to the unhydrolyzed separated fiber solids;
   (iii) re-suspending the unhydrolyzed separated fiber solids in an aqueous solution to produce a re-suspended slurry; and
   (iv) continuing the hydrolysis of the re-suspended slurry to produce the hydrolysis product comprising glucose.

2. The process according to claim 1, wherein, in the step of partially-hydrolyzing (step (i)), the aqueous slurry has a suspended or undissolved fiber solids content of about 3% to about 30% (w/w).

3. The process according to claim 1, wherein the unhydrolyzed fiber solids are separated by microfiltration, centrifugation, vacuum filtration or pressure filtration.

4. The process according to claim 3, wherein the unhydrolyzed solids are separated by microfiltration.

5. The process according to claim 1, wherein the aqueous slurry is concentrated prior to the step of partially-hydrolyzing (step (i)).

6. The process according to claim 1, wherein the process is carried out in a hydrolysis system comprising one or more than one hydrolysis reactor selected from the group consisting of an agitated tank, an unmixed tank, an agitated tower and an unmixed tower.

7. The process according to claim 6, wherein the agitated tower is an upflow tower.

8. The process according to claim 6, wherein the unmixed tower is an upflow tower.

9. The process according to claim 1, wherein the process is a batch process.

10. The process according to claim 1, wherein the process is a continuous process.

11. The process according to claim 1, wherein about 70% to about 100% of cellulose in the aqueous slurry is converted to glucose.

12. The process according to claim 1, wherein a stream comprising glucose produced in step (i) is combined with a stream comprising glucose produced in step (iv) to produce a combined sugar stream.

13. The process according to claim 1, wherein, in the step of partially-hydrolyzing (step (i)), the pretreated lignocellulosic feedstock is obtained from wheat straw, oat straw, barley straw, corn stover, soybean stover, canola straw, rice straw, sugar cane, bagasse, switch grass, reed canary grass, cord grass, or miscanthus.

14. The process according to claim 1, wherein, in the step of partially-hydrolyzing (step (i)), the cellulase enzymes are added at a dosage of about 1.0 to about 40.0 IU per gram of cellulose.

15. The process according to claim 1, wherein, in the step of partially-hydrolyzing (step (i)), the at least one β-glucosidase enzyme is added at a dosage of about 35 to about 200 IU per gram of cellulose.

16. The process according to claim 1, wherein, in the step of partially-hydrolyzing (step (i)), the cellulase enzymes are produced by *Aspergillus, Humicola, Trichoderma, Bacillus, Thermobifida*, or a combination thereof.

17. The process according to claim 1, wherein, in the step of partially-hydrolyzing (step (i)), the β-glucosidase enzyme is produced by *Aspergillus, Humicola, Trichoderma, Bacillus, Thermobifida*, or a combination thereof.

18. The process according to claim 17, wherein the β-glucosidase enzyme is produced by *Aspergillus* or *Trichoderma*.

19. The process according to claim 1, wherein the step of continuing the hydrolysis (step (iv)) is carried out for about 12 to about 200 hours.

20. The process according to claim 1, wherein the step of partially hydrolyzing (step (i)) is carried out for about 12 to about 24 hours.

21. The process according to claim 1, wherein, in the step of partially-hydrolyzing (step (i)), about 75% to about 100% (w/w) of the total cellulase enzymes present bind to fiber solids present in the aqueous slurry.

22. The process according to claim 1, wherein, in the step of re-suspending (step (iii)), the aqueous solution is process water.

* * * * *